United States Patent
Skylar-Scott et al.

(10) Patent No.: US 12,296,069 B2
(45) Date of Patent: May 13, 2025

(54) TISSUE CONSTRUCT, METHODS OF PRODUCING AND USING THE SAME

(71) Applicant: President and Fellows of Harvard College, Cambridge, MA (US)

(72) Inventors: Mark Skylar-Scott, Brookline, MA (US); Sebastien Uzel, Cambridge, MA (US); Jennifer Lewis, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 947 days.

(21) Appl. No.: 16/649,056

(22) PCT Filed: Sep. 20, 2018

(86) PCT No.: PCT/US2018/051901
§ 371 (c)(1),
(2) Date: Mar. 19, 2020

(87) PCT Pub. No.: WO2019/060518
PCT Pub. Date: Mar. 28, 2019

(65) Prior Publication Data
US 2020/0289709 A1 Sep. 17, 2020

Related U.S. Application Data

(60) Provisional application No. 62/561,477, filed on Sep. 21, 2017.

(51) Int. Cl.
| | |
|---|---|
| *A61L 27/38* | (2006.01) |
| *A61B 5/00* | (2006.01) |
| *A61L 27/22* | (2006.01) |
| *A61L 27/36* | (2006.01) |
| *A61L 27/44* | (2006.01) |
| *A61L 27/50* | (2006.01) |
| *A61L 27/54* | (2006.01) |
| *B33Y 10/00* | (2015.01) |
| *B33Y 80/00* | (2015.01) |
| *C12N 5/071* | (2010.01) |

(52) U.S. Cl.
CPC ......... *A61L 27/3895* (2013.01); *A61L 27/222* (2013.01); *A61L 27/227* (2013.01); *A61L 27/3633* (2013.01); *A61L 27/3808* (2013.01); *A61L 27/3826* (2013.01); *A61L 27/3891* (2013.01); *A61L 27/44* (2013.01); *A61L 27/507* (2013.01); *A61L 27/54* (2013.01); *B33Y 10/00* (2014.12); *B33Y 80/00* (2014.12); *C12N 5/0697* (2013.01); *A61B 5/686* (2013.01); *A61L 2430/02* (2013.01); *A61L 2430/04* (2013.01); *A61L 2430/10* (2013.01); *A61L 2430/14* (2013.01); *A61L 2430/16* (2013.01); *A61L 2430/20* (2013.01); *A61L 2430/22* (2013.01); *A61L 2430/26* (2013.01); *A61L 2430/28* (2013.01); *A61L 2430/30* (2013.01); *A61L 2430/32* (2013.01); *A61L 2430/40* (2013.01); *C12N 2502/28* (2013.01); *C12N 2506/45* (2013.01); *C12N 2513/00* (2013.01); *C12N 2533/54* (2013.01); *C12N 2533/56* (2013.01); *C12N 2533/72* (2013.01); *C12N 2533/74* (2013.01); *C12N 2533/76* (2013.01); *C12N 2533/78* (2013.01); *C12N 2533/80* (2013.01)

(58) Field of Classification Search
None
See application file for complete search history.

(56) References Cited

U.S. PATENT DOCUMENTS

| | | | |
|---|---|---|---|
| 2011/0001869 A1 | 1/2011 | Hideyuki | |
| 2015/0050686 A1* | 2/2015 | Sheth | C12M 33/00 435/29 |
| 2015/0321424 A1 | 11/2015 | Pridoehl et al. | |
| 2015/0330970 A1 | 11/2015 | Lancaster | |
| 2016/0130558 A1 | 5/2016 | Baer | |
| 2016/0279868 A1* | 9/2016 | Burdick | B33Y 70/00 |
| 2016/0287756 A1 | 10/2016 | Lewis et al. | |
| 2016/0288414 A1 | 10/2016 | Ozbalat et al. | |
| 2017/0067014 A1 | 3/2017 | Takebe et al. | |
| 2017/0355945 A1 | 12/2017 | Kamm et al. | |
| 2018/0030409 A1 | 2/2018 | Lewis et al. | |
| 2018/0110901 A1 | 4/2018 | Lewis et al. | |

FOREIGN PATENT DOCUMENTS

| | | |
|---|---|---|
| CA | 2881796 A1 | 2/2014 |
| CN | 1592781 A | 3/2005 |
| CN | 105324136 A | 2/2016 |

(Continued)

OTHER PUBLICATIONS

"Filament." Merriam-Webster.com Dictionary, Merriam-Webster, https://www.merriam-webster.com/dictionary/filament. Accessed Mar. 1, 2024. (Year: 2024).*

(Continued)

*Primary Examiner* — Allison M Fox
(74) *Attorney, Agent, or Firm* — Crowell & Moring LLP

(57) ABSTRACT

Described are methods for producing tissue constructs, tissue constructs produced by the methods, and their use. The described method of producing a tissue construct comprises providing a granular tissue, depositing one or more filaments on or in the granular tissue, each filament comprising an ink, and gelling or fusing the granular tissue, thereby producing the tissue construct.

36 Claims, 17 Drawing Sheets
(13 of 17 Drawing Sheet(s) Filed in Color)

(56) References Cited

FOREIGN PATENT DOCUMENTS

| | | |
|---|---|---|
| SE | 199901523 | 4/1990 |
| WO | WO 03/022988 A2 | 3/2003 |
| WO | WO 2011/055855 A1 | 5/2011 |
| WO | WO 2014/209994 A2 | 12/2014 |
| WO | WO 2015/069619 A1 | 5/2015 |
| WO | WO 2015/073944 A2 | 5/2015 |
| WO | WO 2016/019087 A1 | 2/2016 |
| WO | WO 2016/141137 A1 | 9/2016 |
| WO | WO 2016/161944 A1 | 10/2016 |
| WO | WO 2016/179016 A2 | 11/2016 |
| WO | WO 2016/179242 A1 | 11/2016 |
| WO | WO2017/049066 * 3/2017 ............ A61K 35/12 |
| WO | WO 2018/048900 A1 | 3/2018 |
| WO | WO 2018/106704 A1 | 6/2018 |
| WO | WO 2018/106705 A1 | 6/2018 |
| WO | WO 2019/018737 A1 | 1/2019 |
| WO | WO 2019/060518 A1 | 3/2019 |

OTHER PUBLICATIONS

Countess(TM) Cell Data Sheet: NIH/3T3 cells, retrieved from URL: chrome-extension://efaidnbmnnnibpcajpcglclefindmkaj/https://www.thermofisher.com/content/dam/LifeTech/migration/en/filelibrary/cell-tissue-analysis/pdfs.par.38126.file.dat/nih-3t3.pdf on May 31, 2024.*

First Office Action and Search Report received in related Chinese Application No. 201880065260.3 dated Sep. 29, 2021 (in Chinese and including English translation).

Lippmann E., et al. "Derivation of blood-brain barrier endothelial cells from human pluripotent stem cells," *Nat Biotechnol*, 30(8):783-791 (2012); the prior version of the article included.

Eiraku M., et al., Self-organized formation of polarized cortical tissues from ESCs and its active manipulation by extrinsic signals, Cell Stem Cell, 3(5):519-32 (Nov. 2008).

Turksen, K., "Adult Stem Cells," *Humana Press*, 2$^{nd}$ ed. (2004)—entire book.

Chrobak, K.M., et al., "Formation of perfused, functional microvascular tubes in vitro," *Microvascular Research*, 71:185-196 (2006).

Hinton, T.J., et al., "Three-dimensional printing of complex biological structures by freeform reversible embedding of suspended hydrogels," *Sci. Adv.*, 1:e1500758, 10 pages (2015).

Kolesky, D.B., et al., "3D Bioprinting of Vascularized, Heterogeneous Cell-Laden Tissue Constructs," *Adv. Mater.*, 26:3124-3130 (2014).

Kolesky, D.B., et al., "Three-dimensional bioprinting of thick vascularized tissues," *PNAS*, 113(12):3179-3184 (2016).

Lancaster, M.A., et al., "Cerebral organoids model human development and microcephaly," *Nature*, 501(7467), 21 pages (2013).

Miller, J.S., "The Billion Cell Construct: Will Three-Dimensional Printing Get Us There?" *PLoS Biol*, 12(6):e1001882, 10 pages (2014).

Miller, J.S., et al., "Rapid casting of patterned vascular networks for perfusable engineered 3D tissues," *Nat. Mater.*, 11(9):768-774 (2012).

Ott, H.C., et al., "Perfusion-decellularized matrix: using nature's platform to engineer a bioartificial heart," *Nature Medicine, Technical Reports*, doi:10.1038/nm1684, 9 pages (2008).

Sato, T., et al., "Long-term Expansion of Epithelial Organoids From Human Colon, Adenoma, Adenocarcinoma, and Barrett's Epithelium," *Gastroenterology*, 141:1762-1772 (2011).

Wu, W., et al., "Omnidirectional Printing of 3D Microvascular Networks," *Adv. Mater.*, 23:H178-H183 (2011).

Highley, C.B., et al., "Direct 3D Printing of Shear-Thinning Hydrogels into Self-Healing Hydrogels," *Adv. Mater.*, 27(34):5075-5079 (2015).

Lian, X. et al., "Robus cardiomyocyte differentiation from human pluripotent stem cells via temporal modulation of canonical Wnt signaling," *PNAS*, E1848-E1857, (2012).

Vrij E. et al., "Directed Assembly and Development of Material-Free Tissues with Complex Architectures," *Adv. Mater.*, 28(21):4032-4039 (2016).

Itoh M., et al., "Scaffold-Free Tubular Tissues Created by a Bio-3D Printer Undergo Remodeling and Endothelialization when Implanted in Rat Aortae," *PLoS One*, 10(9), 15 pages (2015).

Notification Concerning Transmittal of International Preliminary Report on Patentability dated Apr. 2, 2020, and International Preliminary Report on Patentability dated Mar. 24, 2020 received in PCT Application No. PCT/US2018/051901.

International Search Report dated Jan. 16, 2019 received in PCT Application No. PCT/US2018/051901.

Written Opinion of the International Searching Authority dated Jan. 16, 2019 received in PCT Application No. PCT/US2018/051901.

Extended European Search Report including supplementary European search report and the European search opinion, received in European Patent Application No. EP 18859555.7, dated May 28, 2021.

Datta, P., et al., "Bioprinting for vascular and vascularized tissue biofabrication," *Acta Biomaterialia*, 51:1-20 (2017).

Homan, K., et al., "Bioprinting of 3D Convoluted Renal Proximal Tubules on Perfusable Chips," *Scientific Reports*, 6(1):13 pgs. (2016).

Jia, W., et al., "Direct 3D bioprinting of perfusable vascular constructs using a blend bioink," *Biomaterials*, 106:58-68 (2016).

Second Office Action received in related Chinese Application No. 201880065260.3 dated Apr. 29, 2022 (in Chinese and including English translation).

Examination Report No. 1 received in related Australian Application No. 2018336901, dated Jul. 5, 2023 (3 pages).

Examination Report No. 2, received in the corresponding Australian Application No. 2018336901, dated Jun. 18, 2024 (3 pages).

First Office Action, received in the corresponding European Application No. 18859555.7, dated Oct. 9, 2024 (5 pages).

* cited by examiner

Strategies for Embedded-EB Printing

Pouring the granular tissue into a mold of arbitrary shape

Printing the granular tissue onto a substrate or into a mold, allowing for further patterning of the granular tissue Printing the granular tissue into a supporting matrix

TISSUE CONSTRUCT, METHODS OF PRODUCING AND USING THE SAME

RELATED APPLICATIONS

The present patent document is a § 371 filing based on PCT Application Serial No. PCT/US2018/051901, filed Sep. 20, 2018, which claims the benefit of the filing date under 35 U.S.C. § 119 (e) of Provisional U.S. Patent Application Ser. No. 62/561,477, filed Sep. 21, 2017, which is are hereby incorporated by reference.

FEDERALLY SPONSORED RESEARCH OR DEVELOPMENT

This invention was made with government support under N00014-16-1-2823 awarded by U.S. Office of Naval Research (NAVY/ONR) and under HG008525 awarded by National Institutes of Health (NIH). The government has certain rights in this invention.

BACKGROUND

The present disclosure is related generally to tissue engineering and more particularly to fabricating tissue constructs, e.g., including embedded vasculature and/or tubules.

The ability to create three-dimensional (3D) vascularized tissues on demand could enable scientific and technological advances in tissue engineering, drug screening, toxicology, 3D tissue culture, and organ repair. To produce 3D engineered tissue constructs that mimic natural tissues and, ultimately, organs, several key components—cells, extracellular matrix (ECM), and vasculature—may need to be assembled in complex arrangements. Each of these components plays a vital role: cells are the basic unit of all living systems, ECM provides structural support, and vascular networks provide efficient nutrient and waste transport, temperature regulation, delivery of factors, and long-range signaling routes. Without perfusable vasculature within a few hundred microns of each cell, three-dimensional tissues may quickly develop necrotic regions. The inability to embed vascular networks in tissue constructs has hindered progress on 3D tissue engineering for decades.

Classical experiments performed half a century ago demonstrated the immense self-organizing capacity of vertebrate cells. Even after complete dissociation, cells can reaggregate and reconstruct the original architecture of an organ. This outstanding feature was used to rebuild organ parts or even complete organs from tissue or embryonic stem cells. Such stem cell-derived three-dimensional cultures are called organoids. Because organoids can be grown from human stem cells and from patient-derived induced pluripotent stem cells, they have the potential to model human development and disease and in a tree-dimensional, biomimetic environment (Lancaster MA, et al., Cerebral organoids model human brain development and microcephaly. Nature 501 (7467):373-9 (2013)). Furthermore, they have potential for drug testing and even future organ replacement strategies (Lancaster et al., 2013).

New methods of creating tissue constructs suitable for studies of tissue development and disease, as well as transplantation are desired.

SUMMARY

Certain embodiments relate to a method of producing a tissue construct, comprising providing a granular tissue; depositing one or more filaments on or in the granular tissue, each filament comprising an ink; and gelling or fusing the granular tissue, thereby producing the tissue construct. The granular tissue comprises approximately 1000 to 1 billion cells per mL of the granular tissue. In the method, the granular tissue may comprise cells in the form of single cells, cell aggregates, or both having diameter in the range from about 10 um to about 5 mm. The ink may comprise one or more sacrificial ink (for vasculature/duct/tubule/gland printing), cell laden ink (for complex patterning of multicellular tissues), structural ink (for support/mechanical cues/actuation), conductive ink (for sensing/actuation/stimulation), optical waveguide (for stimulation/optogenetics). The method may further comprise removing the ink to create one or more open channel or void, and exposing the one or more open channel or void to fluid perfusion. In the method, the depositing step is to form a functional vascular channel network on or in the granular tissue. The granular tissue may comprise one or more of organoids, embryoid bodies, cell spheroids, and multicellular tissue aggregates. The granular tissue may further include at least one of gelatin, hyaluronic acid, agarose, alginate, poly(ethylene-glycol), native extracellular matrix blends to act as a filler, porogen, drug delivery vehicles, sensors, actuators, photoresponsive elements, or a rheological modifier. The step of providing a granular tissue comprises growing a plurality of cells; collecting the plurality of cells; and compacting the cells to form the granular tissue. The step of providing the granular tissue may further comprise aggregating the plurality of cells into granular tissue following the growing and collecting steps. In the method, the growing step nay be on a substrate or in a suspension culture. The substrate is a microwell array. The step of providing the granular tissue may further comprise pouring the granular tissue into a mold of arbitrary shape. The step of providing the granular tissue may further comprise printing the granular tissue onto a substrate for further pattering of the granular tissue. The step of providing the granular tissue may further comprise printing the granular tissue into or onto a supporting matrix, such as another granular tissue, an acellular matrix or a mixture of the two, allowing for further patterning of the granular tissue construct. The supporting acellular matrix may include gelatin, collagen, Matrigel, fibrin, Carbopol, Pluronics, hyaluronic acid, agarose, alginate, poly(ethylene-glycol), native extracellular matrix blends, polyacrylic acid, to act as a filler, porogen, drug delivery vehicles, sensors, actuators, photoresponsive elements, or a rheological modifier. The step of providing the granular tissue may further comprise mixing the cells with an extracellular matrix material solution. The extracellular matrix material solution may include any natural or synthetic solution capable of residing in an extracellular space of the granular tissue. The extracellular matrix material solution may comprise one or more of gelatin, fibrin, collagen, and gelatin methacrylate, Matrigel, alginate, chitosan, polyethylene glycol, collagenase sensitive polyethylene glycol, laminin, collagen IV, fibronectin, vitronectin, hyaluronic acid, agarose, cellulose, hydroxyapatite, fibroin, and any modified versions thereof. In the method, the one or more filaments, flow channels or voids are in communication with one or more external devices. The external devices comprise one or more of a pump, a light guide, an actuator, a motor control board, a microcontroller, a data acquisition board, and a field-programmable gate array. In the method, the filaments may comprise a functional vascular channel network on or in the granular tissue, the functional vascular channel network comprising flow channels in fluid communication with an external pump for direct perfusion of oxygen and nutrients after removal of the fugitive ink. The step of exposing the one or more filaments to fluid perfusion is under a fluid shear stress (FSS), wherein the FSS may be pulsed to mimic blood pressure changes during regular heart beats. The method may further include exposing the tissue construct to one or more biological agents, a biological agent gradient, a pressure, and/or an oxygen tension gradient. The method may further include, after removing the ink, injecting a suspension of endothelial cells into the one or more open channels or voids. In the method, each filament may further comprise one or more concentric and coaxial fugitive ink layers. The concentric ink layers may be arranged as a sacrificial core, a shell comprising smooth muscle cells, and a fibroblast outer shell. Alternatively, the concentric ink layers may be arranged as a sacrificial core, an endothelial cell laden inner shell, a shell comprising smooth muscle cells, and a fibroblast outer shell. The step of removing the ink comprises warming the one or more filaments. The step of gelling or fusing the granular tissue may comprise warming the granular tissue, or exposing the tissue to light to induce crosslinking. In the method, the one or more filaments may be extruded through a single printhead before being deposited on or in the granular tissue. Alternatively, the one or more filaments may be extruded through multiple printheads before being deposited on or in the granular tissue. The depositing may be by printing, wherein the print speed is varied while the ink flow is maintained at a constant flow rate, enabling a smooth variation of vascular diameters. Alternatively, the depositing may be by printing, wherein the extrusion rate is varied while the print speed is maintained constant enabling a smooth variation of vascular diameters. The method may further include depositing one or more structural filaments layer by layer on a substrate to form a mold prior to and/or concomitant with the step of providing the granular tissue. The mold may comprise flow channels in fluid communication with the channels or voids for perfusion thereof after removal of the ink. The mold may be 3D printed with one or more integrated inlets and outlets for interfacing with a pump. In the method, the channels or voids may have the same or varying diameters.

Other embodiments relate to a tissue construct produced by the method described above and herein. The tissue construct may be a heart, artery, vein lymphatic vessel, liver, biliary tract, kidney, pancreas, spleen, lymph node, bone, muscle, brain, spinal cord, nerve, ear, eye, skin, subcutaneous tissue, breast, mammary gland, muscle, tendon, diaphragm, myeloid, lymphoid, nose, nasopharynx, larynx, trachea, bronchus, lung, mouth, salivary gland, tongue, oropharynx, laryngopharynx, esophagus, stomach, small intestine, colon, rectum, anus, genitourinary tract, ureter, bladder, urethra, uterus, vagina, vulva, ovary, placenta, scrotum, penis, prostate testicle, seminal vesicle, pituitary, pineal, thyroid, parathyroid, adrenal, and islets of Langerhans.

Further embodiments, relate to the use of the tissue construct produced by the described method for suturing into a body.

Further embodiments, relate to the use of the tissue construct produced by the described method for maturation in vitro.

Further embodiments, relate to the use of the tissue construct produced by the described method in drug toxicity studies.

Further embodiments, relate to the use of the tissue construct produced by the described method in drug screening applications.

Further embodiments, relate to the use of the tissue construct produced by the described method for disease modeling.

Further embodiments, relate to the use of the tissue construct produced by the described method for mechanistic studies.

DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
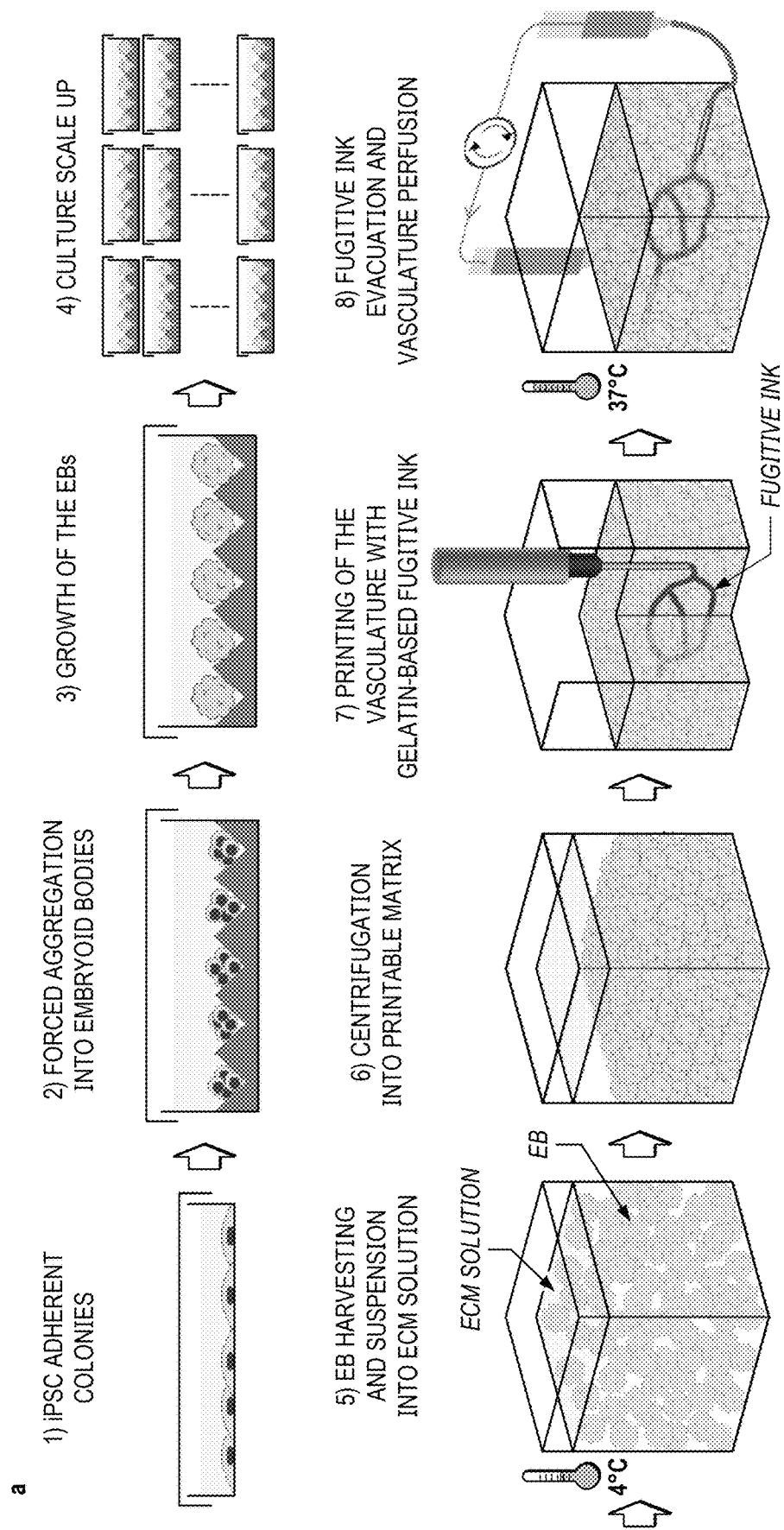
FIG. 1 illustrates scalable embedded direct ink writing of vascular networks into cell-dense granular tissues: (a) Step-by-step illustration of the described process. (b) (i) Microwell culture of (ii) dense tissue aggregate, compacted to form an (iii) tissue matrix. (c) Time-lapse of sacrificial ink (red) writing via embedded 3D printing within an embryoid body matrix. (d) Examples of tissue spheroids taking the form of embryoid bodies or any other differentiated aggregates, such as cerebral or hepatic organoids or cardiac spheroids.
Figure 1:
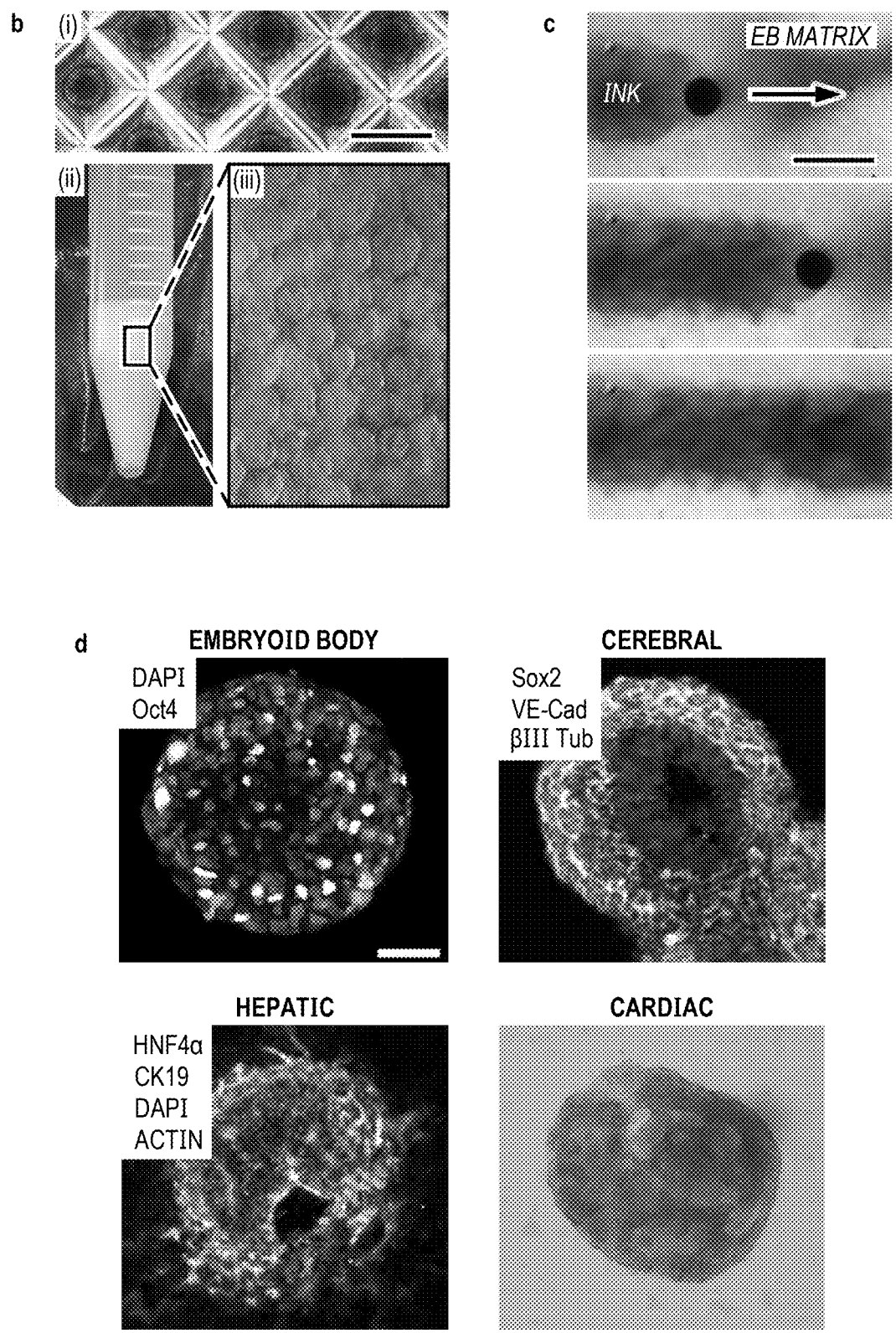

All patents, patent applications and publications, and other literature references cited herein are hereby incorporated by reference in their entirety. The disclosures of these publications in their entireties are hereby incorporated by reference into this application in order to more fully describe the state of the art as known to those skilled therein as of the date of the invention described and claimed herein.

PCT Publication Nos. WO 2015/069619, WO 2016/141137, WO 2016/019087, WO 2016/179242, WO 2018/106704, WO 2018/106705, and WO 2018/048900; and U.S. Pub. Nos. US 2016-0287756 A1, US 2018-0030409 A1, and US 2018-0110901 A1 all are hereby incorporated by reference in their entirety. Also, International Application No. PCT/US18/43042, filed Jul. 20, 2018, entitled "Methods of producing tubular multi-layered tissue constructs," is hereby incorporated by reference in its entirety.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, compositions, devices and materials are described herein.

As used herein and in the appended claims, the singular forms "a," "and," and "the" include plural referents unless the context clearly dictates otherwise. Thus, for example, reference to "a protein" includes a plurality of such proteins and reference to "the progenitor cell" includes reference to one or more progenitor cells known to those skilled in the art, and so forth.

Engineering an organ-specific tissue with therapeutic potential requires overcoming three major challenges. The first challenge includes reaching a critical scale of approximately one billion cells to provide the human body with the necessary level of the secretory, metabolic or filtration activity relative to the organ of interest [1]. The second challenge includes forming a bulk tissue with dense and complex organization that gives rise to the cellular microarchitecture responsible for organ function, while minimizing the engineered tissue footprint. Third challenge is composing and maturing the newly formed tissue with the relevant variety of fully differentiated functional cells.

The first two challenges motivate the need for a percolative vasculature capable of supplying the tissue with oxygen and nutrient necessary for its survival and proper function. Many techniques have been employed to vascularize tissues, including pin casting [2], which, while capable of lumen formation with high fidelity, cannot generate hierarchical branched architectures necessary for efficient nutrient distribution through a tissue and for suturability for tissue transplantation. Alternatively, recellularization of decellularized tissues [3] has been proposed to provide accurate chemical and physical organ templates, yet the reintroduction of cells to the scaffold to achieve physiologic cellular density and complexity has proven challenging. For its ability to generate branching hierarchical networks with clinically-relevant numbers of inlets and outlets, bioprinting can address the challenges of vascularizing engineered organs [4-6]. In particular, embedded printing, which consists of extruding sacrificial filaments within a matrix bath in order to generate free form perfusable vessels [7-9] can enable truly complex 3D vascular networks to be manufactured within the bulk of a matrix.

The second and third challenges call for the use of induced pluripotent stem cells (iPSC)-derived organoids, whose dense nature and their potential to recapitulate cellular complexity, microarchitectures, and functions similar to their in vivo organ counterparts, renders them the ideal tissue building block for therapeutic scale organs [10-12]. Moreover, the common starting structure in most organoid formation assays is the embryoid body (EB), which is amenable to the development of a universal tissue manufacturing method, a priori irrespective of the organ of choice. Although avascular, and therefore non-scalable, past studies have also demonstrated that compact cell spheroids, similar in shape to organoids, can be assembled into structurally sound tissues [13,14].

Printed tissue constructs, including, for example, an interpenetrating vasculature, and methods of printing the tissue constructs using the embedded printing approach are described herein. This embedded printing approach enables, for example, free-form printing of vasculature into dense tissues, and provides a means to maintain tissue viability in a system with unprecedented scale and cellular density. As a result of the cell density and high viability, it is anticipated that these tissues will exhibit remarkable levels of function when differentiated. Specifically, the printed tissue constructs described herein can exhibit many of the native features of the tissue from which their cells are derived. The tissue constructs produced by the methods described herein can be used, for example, for grafting into a patient or for in vitro testing. Other uses of the tissue construct produced by the methods described herein are also contemplated.

Figure 14:
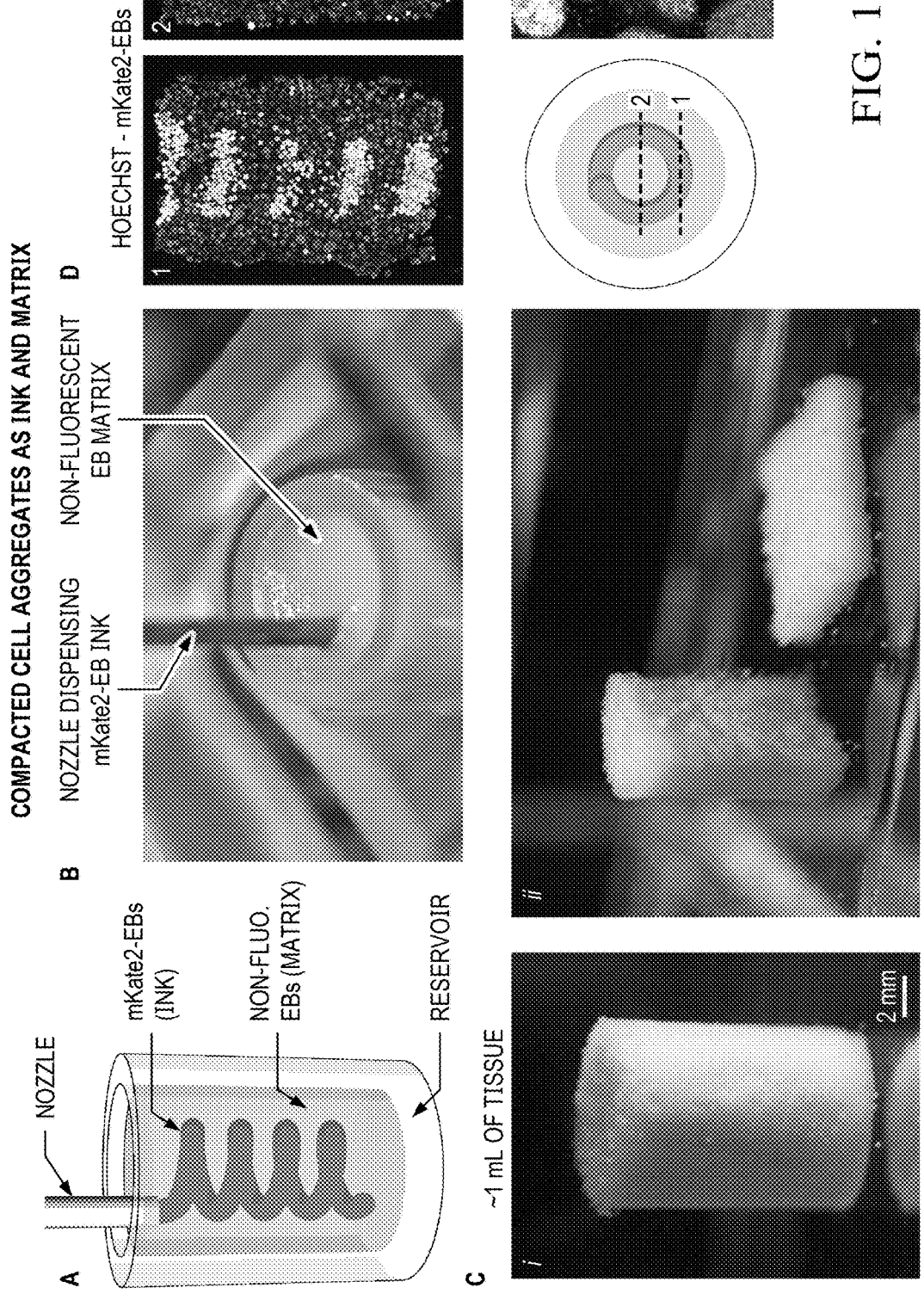
FIG. 14 depicts an example of printing an embryoid body-based ink into an embryoid-body based matrix. (a) Diagram of the printed cell aggregate helix (red) into the cell-aggregate matrix (yellow). (b) A photograph of the nozzle embedded printing into the matrix. Note that the exit of the nozzle is below the surface of the EB matrix. (c) After gelation, the patterned tissue can be removed from the holder and sectioned. (d) cross-sectional epifluorescence views of the tissue, demonstrating the helical pattern of printed cells.

In combining embedded 3D printing and the granular nature of, e.g., iPSC-derived organoids, a method that uniquely address the challenge of generating highly cellular and scalable functional organ-specific tissues is described. Surprisingly, it was demonstrated that a compacted assembly of embryoid bodies or organoids (i.e., "granular tissue") possess rheological properties suited to serve as an embedded printing matrix in which vasculature can be directed patterned and subsequently perfused. Also, surprisingly, the same granular tissue can serve as a printing ink that can be used to print cells onto a substrate, into a mold, or into a supporting matrix such as another granular tissue. Specifically, in certain embodiments, the compacted cell aggregate matrix or the granular tissue can also serve as an ink that can be directly printed to form filaments of dense tissue, or embedded printed with the same or another type of compacted cell aggregate (as illustrated in FIG. 14).

As such, certain embodiments relate to a method of producing a tissue construct, comprising providing a granular tissue (to function, e.g., as the "embedded printing matrix"); depositing one or more filaments on or in the granular tissue, each filament comprising an ink; and gelling or fusing the granular tissue, thereby producing the tissue construct. A schematic of the exemplary method of producing tissue constructs described herein in shown in FIG. 1(a). This is described in detail below.

The term "tissue construct," generally, refers to any engineered tissue or organ, such as a blood vessel, or a more complex construct, such as a kidney or intestine with interpenetrating vasculature. An exemplary tissue construct may be a multi-layered tissue construct (e.g., tubular tissue construct), and can include anywhere from 2 to 8 concentric and/or coaxial cell layers.

The described method includes a step of providing a granular tissue (FIG. 1a (1-6)).

The term "granular tissue," in the context of the tissue constructs and inks, and methods described herein, refers to a material comprising cells either with or without an extracellular matrix, wherein the cells are single cells or aggregates of cells. The granularity arises from the relatively weak interactions between cells or aggregates, enabling them to move relative to each other should a sufficient shear force (greater than the yield stress of the material) be applied, thus inducing a flow. An exemplary material property of granular tissue is that it may exhibit a yield stress, behaving as a Bingham fluid, and be able to flow around a cylinder that is translated through the material, and self-heal behind the cylinder. Below the yield stress, the storage modulus would be greater than the loss modulus, wherein the granular tissue behaves solid-like. The term "granular tissue" further includes structures, such as organoids, embryoid bodies, cell spheroids, multicellular tissue aggregate, or combinations thereof, etc. In general, several terms are used to refer to the culture of well-rounded 3D tissue construct structures: organoids, spheroids, and spheres.

The granular tissue includes approximately 1,000 to 1 billion cells per mL (1K-1 BB cells/mL; "cell density") of the granular tissue. This correspond to an aggregate density of about 100-100 MM aggregates per mL. The granular tissue includes cells in the form of single cells, cell aggregates, or both having diameter in the range from about 10 um to about 5 mm. The granular tissue can be composed of a heterogeneous population of cells and or aggregates, and each aggregate can be composed of one or more cell types.

The term "organoid" refers to a three-dimensional tissue culture, mini organ-like, created or synthesized by culturing one or several types of cells, e.g., human pluripotent or multipotent stem cells on, e.g., a substrate that have undergone a degree of differentiation. As the cells undergo differentiation, the organoid proceeds through several stages of development. Organoids or vesicles have anatomical features that resemble mammalian organs, such as tubule structures, renal structures (e.g., "renal organoids" or vesicles).

The term "embryoid bodies" refers to three-dimensional aggregates of pluripotent stem cells. The pluripotent cell types that comprise embryoid bodies include embryonic stem cells (ESCs) derived from the blastocyst stage of embryos from mouse (mESC), primate, or human (hESC) sources. Additionally, EBs can be formed from embryonic stem cells derived through alternative techniques, including somatic cell nuclear transfer or the reprogramming of somatic cells to yield induced pluripotent stem cells (iPS). Similar to ESCs cultured in monolayer formats, ESCs within embryoid bodies undergo differentiation and cell specification along the three germ lineages—endoderm, ectoderm, and mesoderm—which comprise all somatic cell types.

The granular tissue may be comprised of multiple types of cells or multiple types of cellular aggregates, each with a different composition of cells. The exemplary cells making up the granular tissue include, but are not limited to, at least one of: pluripotent stem cells (e.g., induced pluripotent stem cells (hiPSCs)), multipotent stem cells, embryonic stem cells (ESCs) (e.g., human embryonic stem cells (hESCs)), progenitor cells, terminally differentiated cells, endothelial cells, endothelial progenitor cells, immortalized cell lines, or primary cells.

There are, generally, several procedures for producing the granular tissue or organ culture systems.

In exemplary method, the embryoid bodies obtained from the stem cell culture can be simply cultivated further with a sufficient nutrient supply and an optional supply of special differentiation and growth factors, until the desired amount and/or the desired development stage has been achieved. For example, the desired development stage may be beating cardiomyocytes (heart), glomerulus and capsule formation (kidney), albumin expression (liver), or cortical plate development (brain).

Alternatively, it may be advantageous to cultivate complete organic bodies of a development stage or parts of them (e.g., with desired structures) together with complete organoid bodies of another development stage or parts of them (e.g., with desired structures) and/or differentiated individual cells derived from them and/or undifferentiated adult stem cells. This could achieve, e.g., a more rapid reproduction of desired cells and/or a more rapid or more specific development of desired structures. In this instance, the different organoid bodies or parts of them and/or the differentiated or undifferentiated cells preferably have the same origin.

In the described method, the step of providing a granular tissue comprises growing a plurality of cells, collecting the plurality of cells, and compacting the cells to form the granular tissue. See, e.g., FIG. 1. Typically, to attain a viscoelastic granular tissue with a measurable yield stress (i.e., a Bingham fluid), the aggregates must be compacted in a bath to a high density (in reference to the term "compacting"). The term "high density" refers to cellular density approaching that found in vivo; i.e., cellular density above about 100 million cells per ml of tissue may be considered high density. This compaction can be performed by taking a low density suspension of aggregates ("low density" refers to the uncompacted, unjammed, aggregate tissue; quantitatively, "low density" may be the equivalent to a cellular density of less than about 50 million cells per ml of tissue) and forcing the aggregates together via centrifugation ("forced aggregation, FIG. 1a(6)), settling by gravity, physical compaction via a syringe, plunger and porous filter, drying, or aggregate growth in a confined space. The step of providing a granular tissue in the described method may further include aggregating the plurality of cells into the granular tissue following the growing and collecting steps. The term "aggregating" refers to combining single cells or small clumps of cells into a larger whole, or aggregate to form cellular aggregates. The aggregation can either be driven by cell-cell interactions, or by the gelation of an extracellular matrix that holds the cells together into an aggregate. The bonds holding the aggregates together are typically larger than the interaggregate bond. Aggregation may occur either by centrifugation of cells into microwells (referred to as "forced aggregation"), a hanging-drop method, plating cells onto a nonadherent substrate, such as an untreated cell culture flask, or by random aggregation that can occur when cells are introduced into a suspension bioreactor culture. The growing may be on a substrate, such as a microwell array, or in a suspension culture.

Figure 12:
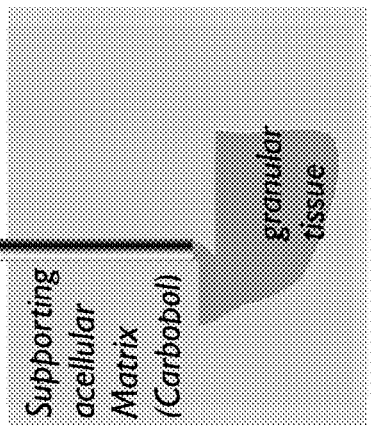
FIG. 12 depicts strategies for embedded embryoid body printing. a) Cell aggregate matrix molding, followed by embedded printing of an ink (red) into the cell aggregate matrix. b) Cell aggregate ink printing into a rigid container, followed by embedded printing of a second ink (red) into the printed cell aggregate ink (i.e., the first ink serves as a matrix for the second ink). c) Embedded printing of a cell aggregate ink into a supporting matrix (such as Carbopol, Alginate, Pluronic, . . . ), followed by embedded printing of a second ink (red) into the printed cell aggregate ink (i.e., the first ink serves as a matrix for the second ink).
Figure 12:
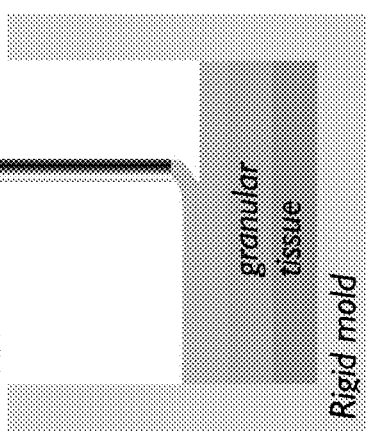
Figure 12:
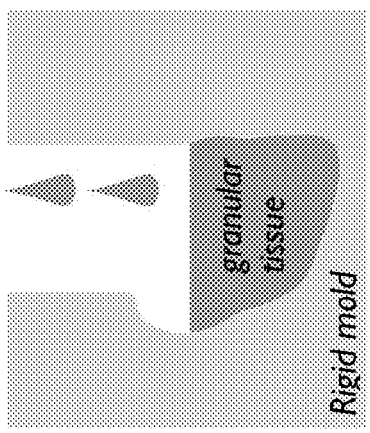
Figure 12:
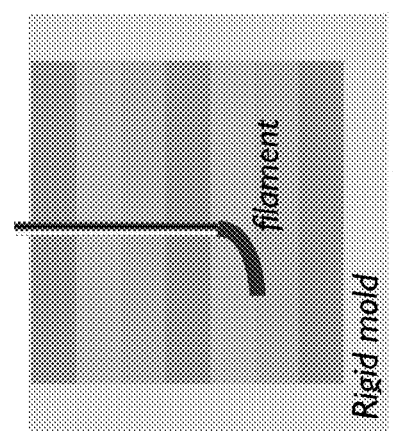
Figure 12:
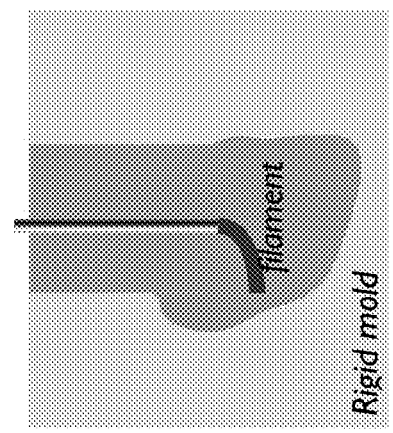

In certain embodiments, the method may further comprise pouring the granular tissue into a mold of arbitrary shape (e.g., FIG. 12, left column). In one example, the mold may be formed of an elastomeric silicone, a structural material known to be viscoelastic, non-toxic, biocompatible, and capable of forming reversible press-to-fit seals. The mold may also have other functionalities besides defining the shape of the tissue construct. For example, the mold may serve as an interface for perfusion of channels in a printed tissue construct.

Alternatively, the method may include printing the granular tissue onto a substrate or into a mold allowing for further patterning of the granular tissue construct (FIG. 12, center column).

Alternatively, the method may include printing the granular tissue into or onto a supporting matrix, such as another granular tissue, an acellular matrix, or a mixture of the two, allowing for further patterning of the granular tissue construct (FIG. 12. right column). This step may also incorporate a mold of arbitrary shape.

The supporting acellular matrix may include gelatin, collagen, Matrigel, fibrin, Carbopol, Pluronics, hyaluronic acid, agarose, alginate, poly(ethylene-glycol), native extracellular matrix blends, polyacrylic acid, to act as a filler, porogen, drug delivery vehicles, sensors, actuators, photoresponsive elements, or a rheological modifier. These materials can either be used in bulk, or rendered into microgels via the use of a mechanical blender, via the application of droplet microfluidics, or via the gelation of small droplets.

The method may further include mixing the cells with an extracellular matrix material solution (FIG. 1a(5)), wherein the extracellular matrix material solution may comprise any natural or synthetic solution capable of residing in an extracellular space of the granular tissue. The extracellular matrix material solution may comprise one or more of, e.g., gelatin, fibrin, collagen, and gelatin methacrylate, Matrigel, alginate, chitosan, polyethylene glycol, collagenase sensitive polyethylene glycol, laminin, collagen IV, fibronectin, vitronectin, hyaluronic acid, agarose, cellulose, hydroxyapatite, fibroin, and any modified versions thereof.

In one exemplary method, to form a granular tissue, including, for example, embryoid bodies, cells may be grown to a specified confluency. In certain embodiments, the preferred cell confluency may be, e.g., 40-80%; 50-80%, or 60-80%. Alternatively, cells may be grown to a specified confluency of at least, e.g., 40%, at least 50%, at least 60%, at least 70%, or at least 80%. Other cell confluency within the specified ranges is also contemplated.

Once the desired confluency of the cells is reached, the cells may be lifted and prepared as a mostly single-cell suspension. Several centrifugation and re-suspension steps may be followed by seeding the cells in wells, which may be centrifuged to compact the cells to form embryonic bodies in the microwells. Details of preferable methods of producing granular tissue are provided in the Examples section below.

Once the embryonic bodies reach approximate size of, e.g., 200-250 μm in diameter (typically 2-4 days in microwell culture), the embryonic bodies can be harvested and prepared in a suitable media (e.g., prepolymer ECM solution), forming a dense embryonic body slurry that can be handled and pipetted in subsequent steps.

In certain embodiments, the embryoid bodies can be pre (before printing) or post (after printing) differentiated into organoids (e.g., kidney, liver, cardiac, cerebral, etc.).

For example, the embryoid bodies can be differentiated into organoids before printing, i.e., before the step of depositing one or more filaments on or in the granular tissue. In certain embodiments, one or more biological agents, a biological agent gradient, pressure, and/or oxygen tension gradient may be used to direct development and differentiation of organoids from the embryonic body(ies), and/or its functioning before printing.

In certain other embodiments, the embryoid bodies can be differentiated into organoids after printing, i.e., after the step of depositing one or more filaments on or in the granular tissue. Similarly, one or more biological agents, a biological agent gradient, pressure, and/or oxygen tension gradient may be used to direct development and differentiation of organoids from the embryonic body(ies), and/or its functioning, but after the step of depositing one or more filaments on or in the granular tissue.

In certain embodiments, embryoid bodies could be composed of primary, iPSC-derived, and/or embryonic stem cells that are then aggregated into cell spheres or spheroids. The terms "spheres" and "spheroids" refer to aggregates of cells that are spherical in shape.

In certain embodiments, the granular tissue may also contain acellular aggregates or granules of, for example, gelatin, hyaluronic acid, agarose, alginate, poly(ethyleneglycol), native extracellular matrix blends to act as a filler, porogen, drug delivery vehicles, sensors, actuators, photoresponsive elements, or a rheological modifier. The term "acellular aggregates" refers to a type of biomaterial derived from processing human or animal tissues to remove cells and retain portions of the material. These materials are typically cell-free.

In certain embodiments, there can be a plurality of embryoid bodies, organoids, spheroids, or combinations thereof that form the granular tissue, into which filaments, e.g., forming vasculature, can be printed via, e.g., embedded 3D printing of inks, such as fugitive inks. Such a plurality may include, e.g., combinations of atrial and ventricular cardiac aggregates, smooth muscle and fibroblast aggregates, forebrain and hindbrain aggregates, ureteric bud and mesonephric mesenchyme organoids.

The described methods also include a step of depositing one or more filaments on or in the granular tissue, each filament comprising an ink (FIG. 1a(7)). In certain embodiments, the ink comprises one or more of sacrificial ink (e.g., for vasculature/duct/tubule/gland printing), cell laden ink (e.g., for complex patterning of multicellular tissues), structural ink (e.g., for support/mechanical cues/actuation), conductive ink (e.g., for sensing/actuation/stimulation), optical waveguide (e.g., for stimulation/optogenetics), or a granular tissue In one embodiment, the compacted cell aggregate matrix or granular tissue can also serve as an ink that can be directly printed to form filaments of dense tissue, or embedded printed with the same or another type of compacted cell aggregate.

In certain embodiments, the depositing may be by printing, such as 3D printing. Methods of printing filaments are known in the art, and were previously described in, e.g., PCT Pub. No. WO 2015/069619, which is incorporated herein by reference in its entirety. Details of 3D printing methods may be found in PCT Pub. Nos. WO 2014/209994 and WO 2015/073944, both of which are hereby incorporated by reference in their entirety.

For example, printing may be by depositing one or more filaments on or in the granular tissue, each filament comprising an ink, to form one or more filament patterns. In certain embodiments, the ink may be removed to create a network of channels on or in the granular tissue.

In certain embodiments, while depositing the filaments by printing on or in the granular tissue, the print speed can be varied while the ink flow is maintained at a constant flow rate, enabling a smooth variation of channel/vascular diameters. Alternatively, while depositing the filaments by printing on or in the granular tissue, the extrusion rate may be varied while the print speed is maintained constant, enabling a smooth variation of channel/vascular diameters.

Each filament may include one or more concentric and coaxial fugitive ink layers. The concentric ink layers may be arranged as a sacrificial core, a shell comprising smooth muscle cells, and a fibroblast outer shell. Alternatively, the concentric ink layers may be arranged as a sacrificial core, an endothelial cell laden inner shell, a shell comprising smooth muscle cells, and a fibroblast outer shell.

In certain embodiments, the one or more filaments may be extruded through a single printhead before being deposited on or in the granular tissue. Alternatively, the one or more filaments may be extruded through multiple printheads before being deposited on or in the granular tissue. Methods of extruding the filaments through single or multiple printheads are known in the art.

In certain embodiments, the described method may further include depositing one or more structural filaments layer by layer on a substrate to form a mold prior to and/or concomitant with the step of providing the granular tissue. The mold may include flow channels in fluid communication with the channels or voids for perfusion thereof after removal of the ink. In certain embodiments, the mold may be 3D printed with one or more integrated inlets and outlets for interfacing with a pump.

The arrangement of the filaments on or in the granular tissue may be continuous or discontinuous. In a continuous arrangement, the filaments of an exemplary filament pattern (and comprising one or more predetermined ink types) may form a single interconnected filament network on or in the granular tissue. For example, a single filament comprising predetermined ink type(s) may be deposited in a single layer or in multiple layers to form the continuous arrangement. Alternatively, a plurality of filaments comprising predetermined ink type(s) may be deposited in a single layer or in multiple layers to form the continuous arrangement, where each of the filaments is in physical contact with, and possibly at least partially coalesced with, another filament comprising the same predetermined ink type(s).

In a discontinuous arrangement of filaments comprising one or more predetermined ink(s), a single interconnected filament network of the predetermined ink type(s) is not formed on or within the granular tissue. Instead, the filaments comprising the predetermined ink type(s) may be dispersed uniformly or nonuniformly on and/or throughout the granular tissue. Consequently, other structures may also be dispersed uniformly or nonuniformly (e.g., in clumps) throughout the granular tissue. In this embodiment, some, all or none of the filaments of a given filament pattern and ink type(s) may be in physical contact with another filament comprising the same ink type(s).

As noted above, in certain embodiments, the granular tissue may function as "a granular tissue matrix," composed of either embryoids or organoids, and may or may not contain additional proteins specifically added to help bind cells, embryoids, and/or organoids together to form a more cohesive matrix for embedded printing. Exemplary proteins or small molecules that may be added to help bind cells include collagen type I, collagen type IV, laminin, fibronectin, fibrin, fibrinogen, gelatin, gelatin methacrylate, hyaluronic acid, hyaluronic acid methacrylate, chondroitin, aggrecan, poly(ethylene-glycol), alginate, alginate methacrylate, fibroin, silk, hydroxyapatite, poly(vinyl-alcohol), poly-lysine, poly-ornithine, agarose, agarose methacrylate, basement membrane extract (Matrigel) or transglutaminase.

In certain embodiments, an ink (e.g., fugitive ink) may be used to create embedded vasculature, which can either be printed directly into the granular tissue matrix or pre-printed, e.g., on a substrate, and then infilled with the granular tissue.

Exemplary printed inks include: sacrificial ink(s) for printing vasculature, duct(s), tubule(s), and/or glands; cell laden ink(s) for printing complex patterning of multicellular tissues; structural ink(s) for printing support, mechanical cues, and actuation; conductive ink(s) for sensing, actuation, and/or stimulation; optical waveguide inks for stimulation and/or optogenetics.

Cell laden inks may include at least one viable cell and may include a large number of viable cells. For example, each of the cell-laden inks may have a cell concentration of at least about 100 cells/ml, at least about 1000 cells/ml, at least about $10^4$ cells/ml, at least about $10^5$ cells/ml, at least about $10^6$ cells/ml, at least about $10^7$ cells/ml, or at least about $10^8$ cells/ml. Typically, the cell concentration is no higher than about $10^9$ cells/ml, or no higher than about $10^8$ cells/ml.

The viable cells and the predetermined cell types may include any mammalian cell type selected from cells that make up the mammalian body, including germ cells, somatic cells, and stem cells. Depending on the type of cell, cells that make up the mammalian body can be derived from one of the three primary germ cell layers in the very early embryo: endoderm, ectoderm or mesoderm. The term "germ cells" refers to any line of cells that give rise to gametes (eggs and sperm). The term "somatic cells" refers to any biological cells forming the body of a multicellular organism; any cell other than a gamete, germ cell, gametocyte or undifferentiated stem cell. For example, in mammals, somatic cells make up all the internal organs, skin, bones, blood and connective tissue. As such, a cell may include any somatic cell isolated from mammalian tissue, including organs, skin, bones, blood and connective tissue (i.e., stromal cells). Examples of somatic cells include fibroblasts, chondrocytes, osteoblasts, tendon cells, mast cells, wandering cells, immune cells, pericytes, inflammatory cells, endothelial cells, myocytes (cardiac, skeletal and smooth muscle cells), adipocytes (i.e., lipocytes or fat cells), parenchyma cells (neurons and glial cells, nephron cells, hepatocytes, pancreatic cells, lung parenchyma cells) and non-parenchymal cells (e.g., sinusoidal hepatic endothelial cells, Kupffer cells and hepatic stellate cells). The term "stem cells" refers to cells that have the ability to divide for indefinite periods and to give rise to virtually all of the tissues of the mammalian body, including specialized cells. The stem cells include pluripotent cells, which upon undergoing further specialization become multipotent progenitor cells that can give rise to functional or somatic cells. Examples of stem and progenitor cells include hematopoietic stem cells (adult stem cells; i.e., hemocytoblasts) from the bone marrow that give rise to red blood cells, white blood cells, and platelets; mesenchymal stem cells (adult stem cells) from the bone marrow that give rise to stromal cells, fat cells, and types of bone cells; epithelial stem cells (progenitor cells) that give rise to the various types of skin cells; neural stem cells and neural progenitor cells that give rise to neuronal and glial cells; and muscle satellite cells (progenitor cells) that contribute to differentiated muscle tissue.

In certain embodiments, filaments including structural ink(s) for printing support, mechanical cues, and actuation may be 3D printed to form one or more uncured structural filaments comprising one or more of silicone, epoxies, esters of acrylic acid, or one of the extracellular matrix compositions provided above. After printing is complete, the structural filament(s) may be cured (e.g. by heating or photopolymerizing) for a suitable time duration (e.g., about one hour or more), after which the mold may exhibit the desired material properties.

The described methods of producing a tissue constructs also include a step of gelling or fusing the granular tissue.

In certain embodiments, the step of gelling or fusing the granular tissue comprises warming the granular tissue, or exposing the tissue to light to induce crosslinking. The term "gelling" refers to a process by which the granular tissue, capable of flowing under a stress in excess of its yield stress, becomes a solid, elastic-like tissue. This increased interaction could arise from the polymerization of an extracellular matrix that surrounds the cells or aggregates, and/or by increased cell-cell bonding (e.g., fusing, or use of a depletant to drive electrostatic interactions) between the aggregates. A gelled granular tissue no longer behaves as a Bingham fluid, and would likely be significantly stiffer. As such, if a cylinder is translated through the material, it will cut the material.

One exemplary mechanism for gelling is for the cells or cell aggregates to fuse together (in reference to the term "fusing"), whereby the intercell or interaggregate bonding increases to a point where the aggregates or cells no longer behave as separate particles, and whereby typically a microscopically visible merging of the two previously separate aggregates can be observed. This bonding mechanism is due to a cell-cell interaction, where the matrix lies between the aggregates. In this manner, the fused aggregates can no longer flow past each other, instead, they behave as a solid. The stiffness of the granular tissue increases and the material no longer self-heals.

In certain embodiments, the depositing step is to form a functional vascular channel network on or in the granular tissue. To do so, in certain embodiments, the described method may further comprise removing the ink to create one or more open channel or void. The channels or voids may have the same, or varying diameters.

In certain embodiments, the one or more open channel or voids can be exposed to fluid perfusion (FIG. 1a(8)).

The step of exposing the one or more filaments to fluid perfusion may be under a fluid shear stress (FSS). The FSS may be pulsed to mimic blood pressure changes during regular heartbeats. The step of removing the ink may comprise warming the one or more filaments. In certain embodiments, after removing the ink, a suspension of endothelial cells may be injected or deposited into the one or more open channels or voids (see, e.g., FIG. 16). In certain embodiments, the removal of the ink allows the entire architecture to be externally perfused, which allows the cells within the granular tissue or the granular tissue matrix to remain viable.

In certain embodiments, single or multiple types of cells may be injected into the vascular channels. In vivo, every blood vessel having a diameter larger than a capillary contains an outer fibrous tissue layer, a smooth muscle layer, and an inner layer of endothelial cells. One or more other types of cells, such as fibroblasts, may be injected into the vascular channels along with the endothelial cells after removing the fugitive ink. Also, the vascular channels may be co-seeded with fibroblasts and HUVECs, two cell types which may self-assemble into stromal and endothelial layers, respectively, mimicking the anatomy of native blood vessels.

In certain embodiments, the endothelial cells may be suspended in the sacrificial ink, where upon melting of that said ink, the endothelial cells would be allowed to adhere to and coat the surface of the lumen templated by the printed ink.

In certain embodiments, in connection with the described method of producing a tissue construct, the one or more filaments, flow channels or voids are in communication with one or more external devices. The exemplary external devices include one or more of a pump, a light guide, an actuator, a motor control board, a microcontroller, a data acquisition board, and a field-programmable gate array. Other external devices are also contemplated.

In certain embodiments, the filaments can include a functional vascular channel network on or in the granular tissue, the functional vascular channel network comprising flow channels in fluid communication with an external pump for direct perfusion of oxygen, nutrients, and/or as well as growth and differentiation factors after removal of the fugitive ink.

Differentiation factors and/or growth factors are known in the art and comprise, e.g., basic fibroblast growth factor (bFGF) for an increased formation of cardiac cells and fibroblasts, vascular endothelial growth factor (VEGF), DMSO and isoproterenol, fibroblast growth factor 4 (FGF4), hepatocyte growth factor (HGF) for an increased formation of cardiac and liver cells, transforming growth factor beta (TGF beta I) for an increased formation of cardiac cells, epidermal growth factor (EGF) for an increased formation of skin cells and cardiac cells, keratinocyte growth factor (KGF) (sometimes together with cortisone) for the formation of keratinocytes, retinoic acid for an increased formation of nerve cells, cardiac cells and kidney cells, beta nerve growth factor (beta-NGF) for an increased formation of brain cells, liver cells, pancreatic cells and kidney cells, bone morphogenic protein (BMP-4) and activin-A for the formation of mesodermal cells, but are not limited to them. In view of the extensive literature on this topic (see, e.g., "*Adult Stem Cells*", editor K. Turksen, Human Press, 2004) those skilled in the art will be readily able to identify and, if necessary, to use other suitable factors depending on the type of cells and/or cell combinations.

In certain embodiments, a perfusion chip may be used to provide for fluid perfusion once the tissue construct is formed. Exemplary perfusion chips were previously described in PCT Pub. No. WO 2016/179016, which is incorporated herein in its entirety. For example, the resulting tissue structure can be immediately perfused with nutrients as well as growth and differentiation factors via a single inlet and outlet on opposite ends of the chip that connect to the channel, e.g., vascular channel or void to ensure survival and maturation of the cells. In a proof-of-principle study, one centimeter thick bioprinted tissue constructs containing human bone marrow MSCs surrounded by connective tissue and supported by an artificial endothelium-lined vasculature, allowed the circulation of bone growth factors and, subsequently, the induction of bone development.

In certain further embodiments, the described method may include an additional step of exposing the tissue construct to one or more biological agents, a biological agent gradient, a pressure, and/or an oxygen tension gradient. Exemplary biological agents include proteins, growth factors, morphogens, lipids, small molecules, antibodies, DNA, and RNA.

In certain embodiments, additional levels of vasculature can be included within the tissue constructs either through controlled self-assembly in the cell aggregates of the granular tissue (e.g., embryoids, organoids, or cell spheroids), or through the introduction of microvasculature within the granular tissue itself.

The term "controlled self-assembly" of vasculature refers to the processes of vasculogenesis or angiogenesis within the cell aggregates to form functional microvascular networks. For example, microvascular networks can be formed via the presence or introduction of endothelial cells around or within the cell aggregates. To form microvasculature, embryoid bodies could be cultured in a manner that gives rise to differentiated endothelial cells that self-assemble via vasculogenesis or angiogenesis. Alternatively, endothelial cells can be mixed with other cell types to form cell spheroids containing endothelial cells. Alternatively, endothelial cells can be formed via the differentiation or transdifferentiation from one cell type into an endothelial cell. Supporting cells, such as fibroblasts, pericytes, or mesenchymal stem cells could be added to stabilize the formation of microvascular networks within the cell aggregates.

In certain embodiment, levels of vasculature can be included within the tissue constructs through the introduction of microvasculature within the granular tissue itself. This can be performed using a higher-resolution, smaller nozzle for directly writing vascular networks between organoids, using a sacrificial ink. Alternatively, endothelial cells can be mixed in with the ECM prepolymer solution, such that angiogenesis or vasculogenesis can form microvasculature in the space between the compacted cell aggregates in the tissue. Supporting cells, such as fibroblasts, pericytes, or mesenchymal stem cells can also be added to the prepolymer gel to stabilize the resulting microvasculature. The endothelium could be added at a cell density from 1-40 million cells/ml. The supporting cells could be added at a cell density from 1-40 million cells/ml.

In an alternative method of producing a tissue construct, the granular tissue composed of, e.g., embryoids or organoids, can be placed into a mold of arbitrary shape or size that contains pre-patterned filament(s) (e.g., vasculature) network(s).

In yet another alternative method of producing a tissue construct, the granular tissue can serve as either the matrix into or onto which filaments can be printed. In other alternative embodiments, the granular tissue can serve as a printing ink that can be used to print cells onto a substrate, into a mold, or into a supporting matrix such as another granular tissue.

Figure 5:
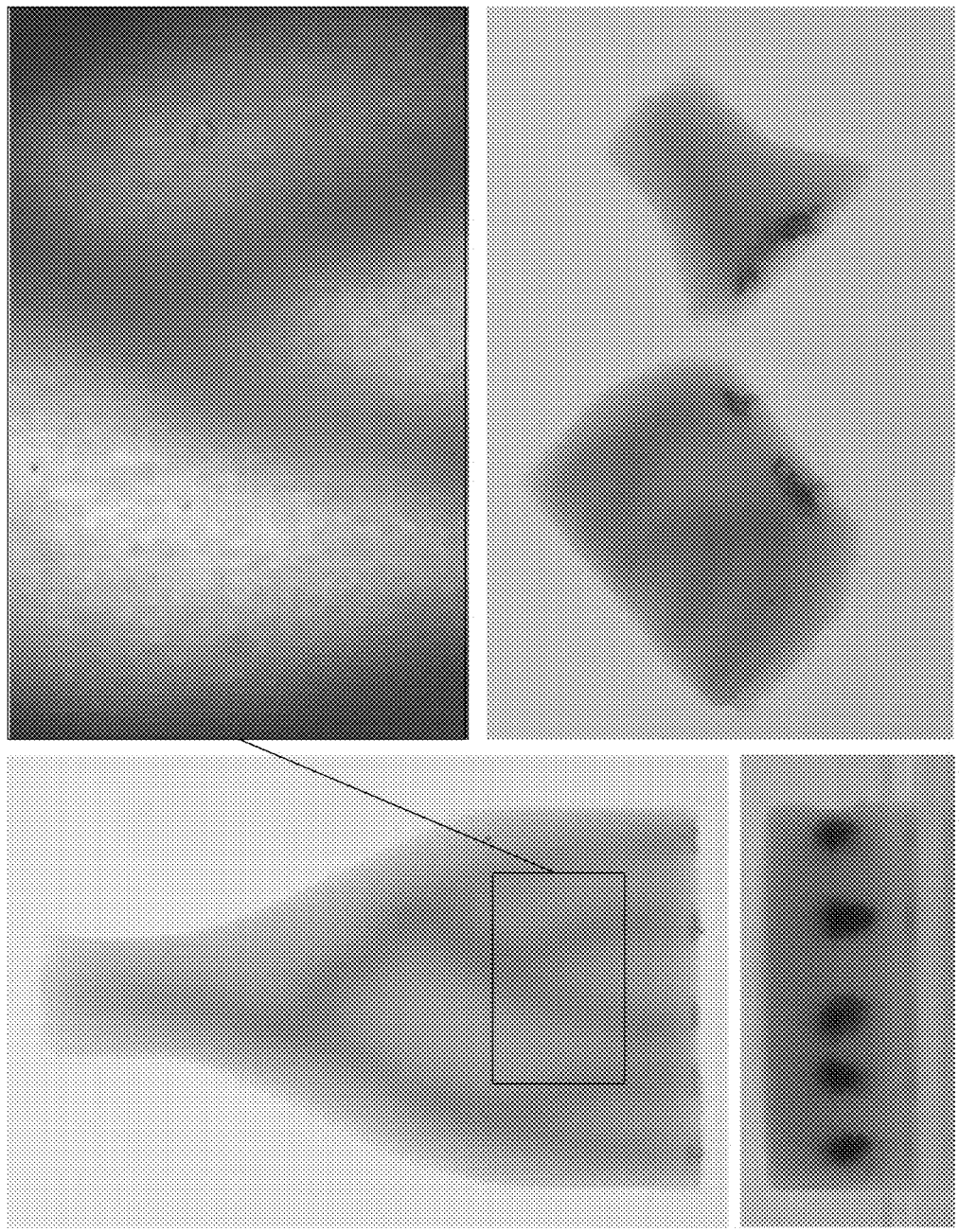
FIG. 5 depicts photographs of a vascularized construct produced by the described method.

FIG. 5 depicts photographs of a vascularized construct produced by the described method.

Figure 6:
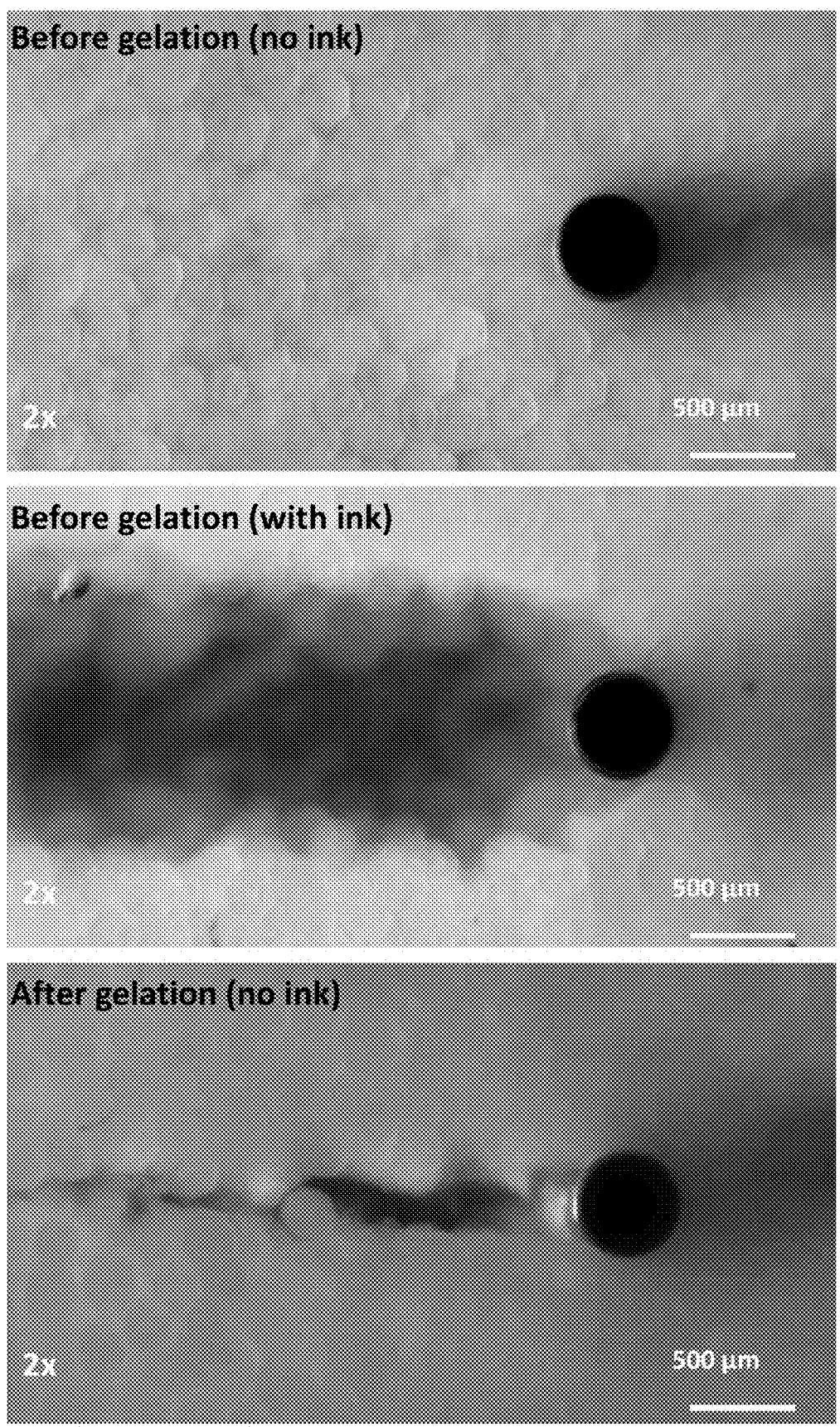
FIG. 6 shows granular tissue before (no ink), before gelation (with ink), and after gelation (no ink).

FIG. 6 shows granular tissue before (no ink), before gelation (with ink), and after gelation (no ink).

Figure 7:
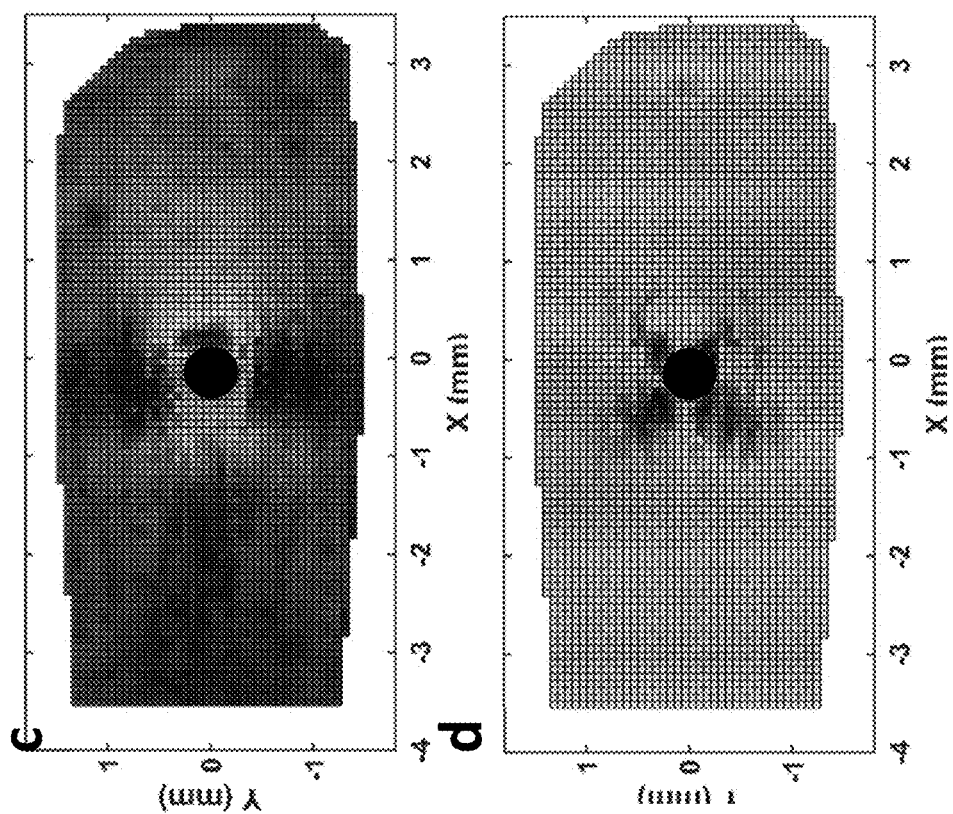
FIG. 7, subfigures (a), (b), (c), and (d) illustrate streamlines and matrix behavior.
Figure 7:
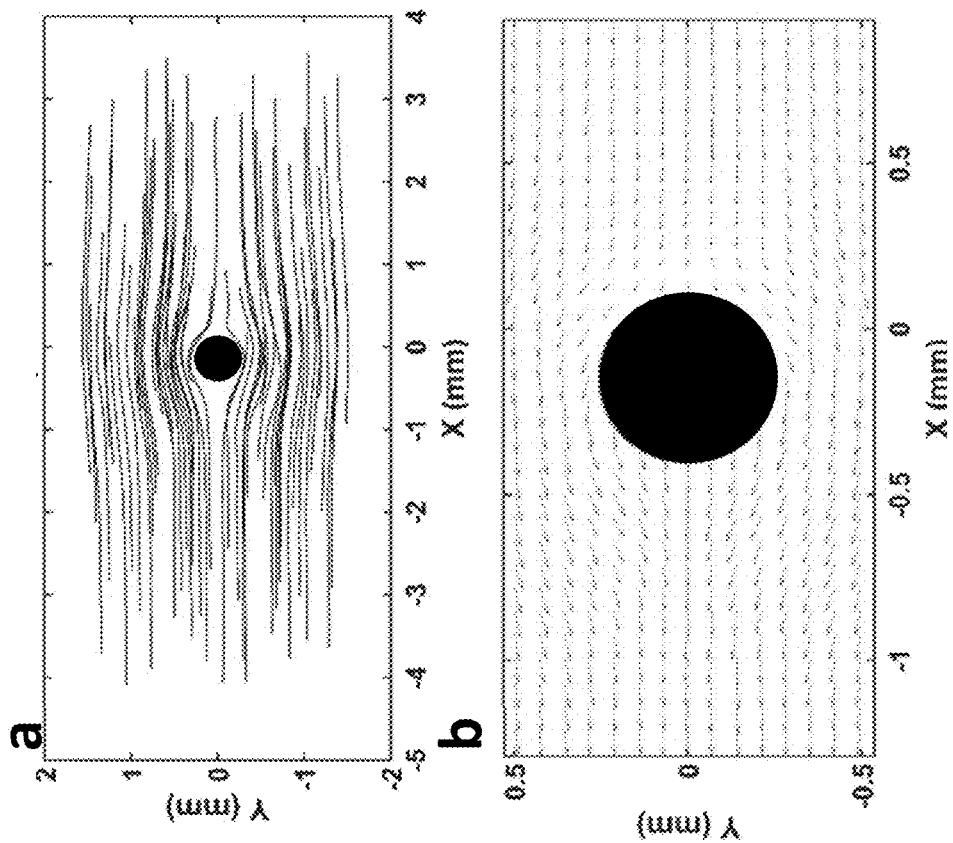

FIG. 7 illustrates streamlines and matrix behavior.

Figure 9:
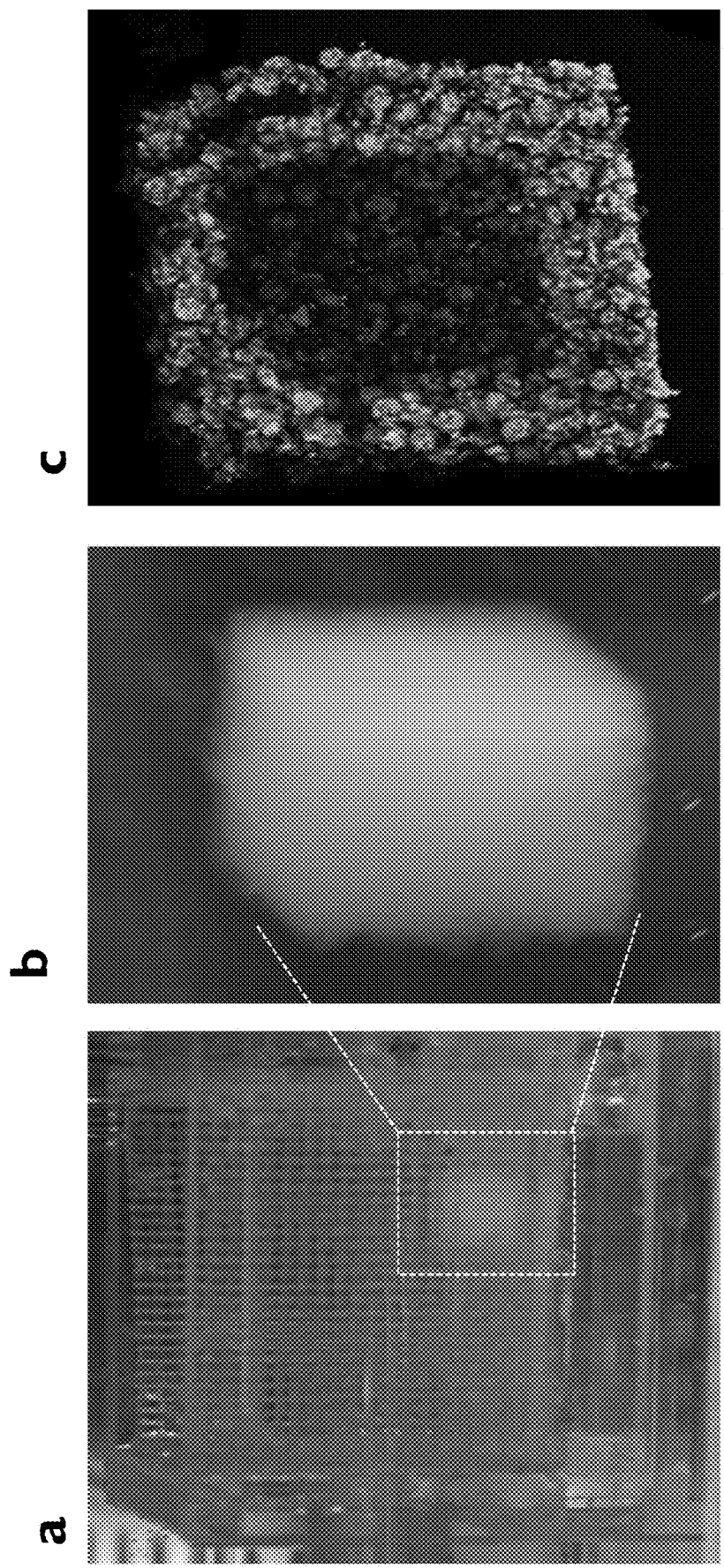
FIG. 9 illustrates viability layer in the absence of perfusion (a)-(c).

FIG. 9 illustrates viability layer in the absence of perfusion.

Figure 10:
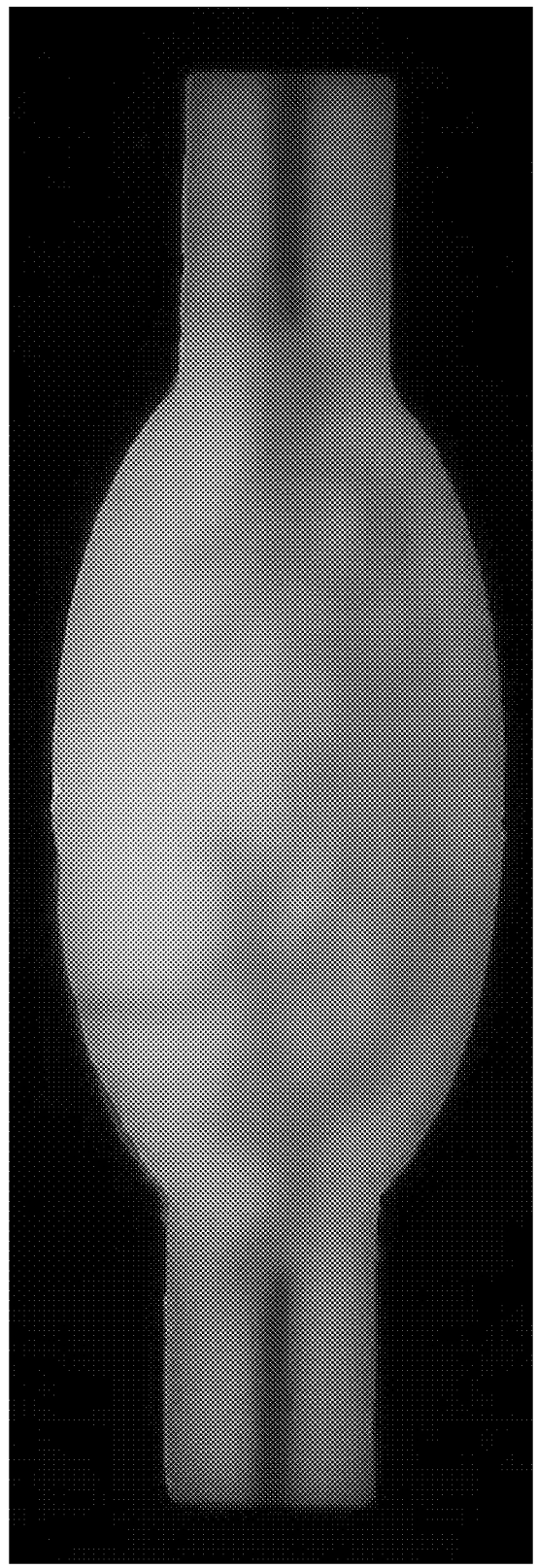
FIG. 10 illustrates an image of printing of the sacrificial ink to form a hierarchical vasculature in a granular tissue.

FIG. 10 illustrates vasculature printing.

Figure 11:
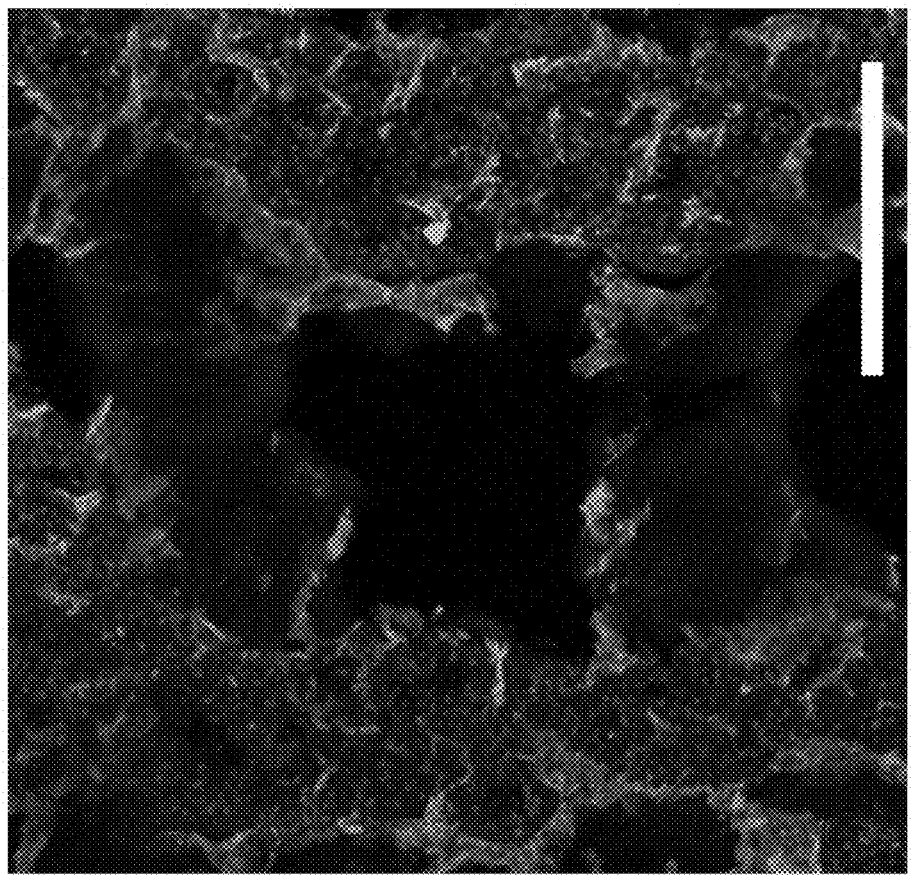
FIG. 11 depicts a longitudinal section and collagen staining after 12 h of tissue perfusion.
Figure 11:
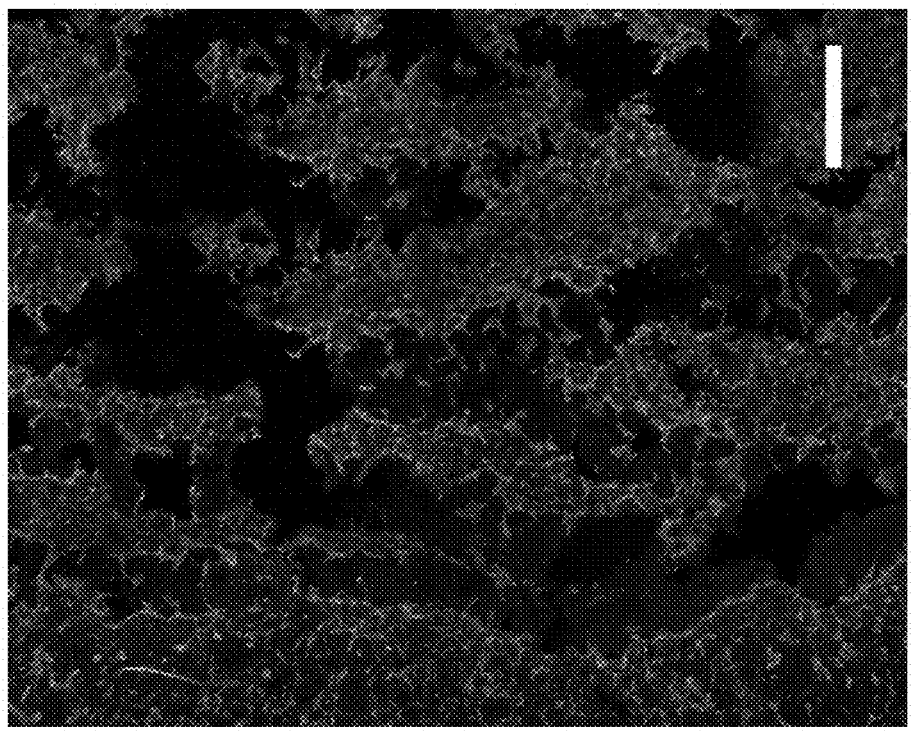

FIG. 11 depicts a longitudinal section and collagen staining after 12 h of tissue perfusion.

FIG. 12 depicts strategies for embedded embryoid body printing. Specifically, in a) cell aggregate matrix molding, followed by embedded printing of an ink (red) into the cell aggregate matrix is shown. In b) cell aggregate ink printing into a rigid container, followed by embedded printing of a second ink (red) into the printed cell aggregate ink (i.e., the first ink serves as a matrix for the second ink) is shown. In c) embedded printing of a cell aggregate ink into a supporting matrix (such as Carbopol, Alginate, Pluronic, . . . ), followed by embedded printing of a second ink (red) into the printed cell aggregate ink (i.e., the first ink serves as a matrix for the second ink) is shown.

Figure 13:
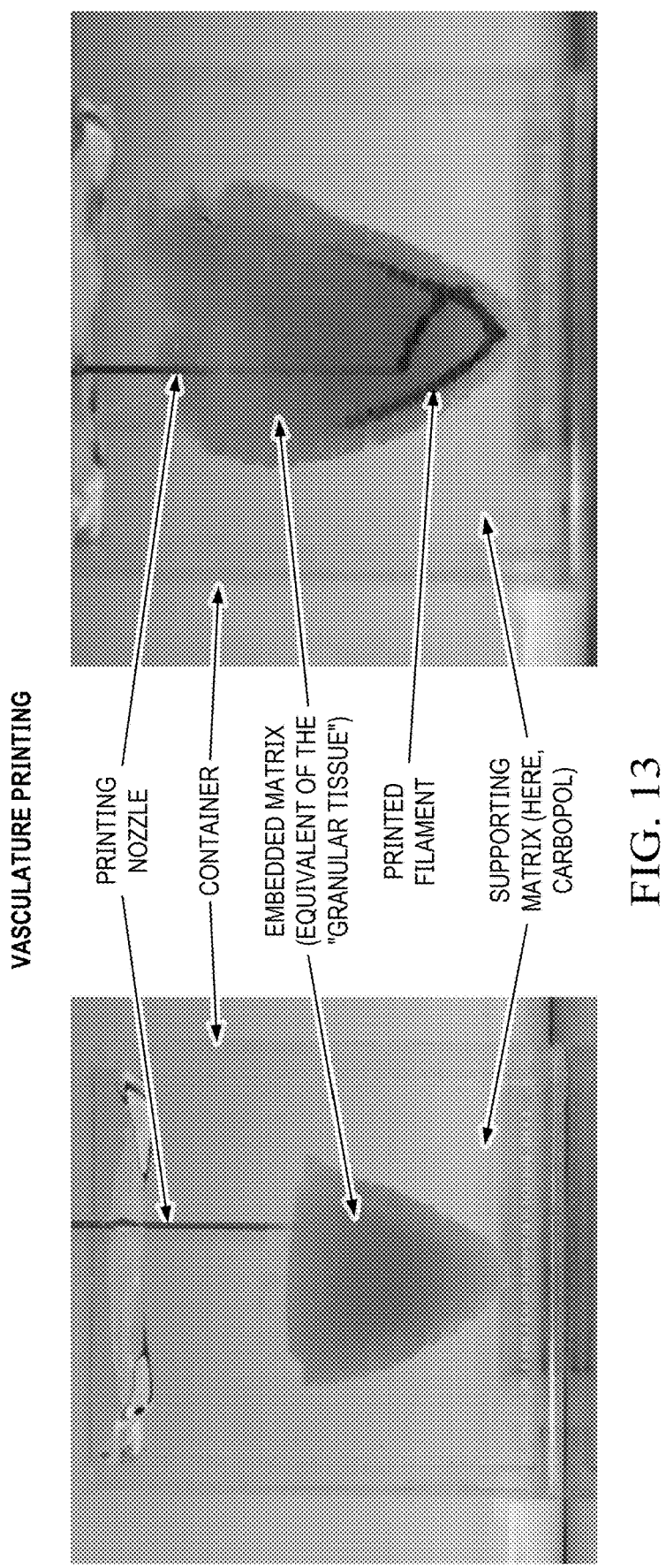
FIG. 13 depicts "organ" shape printing process, illustrating the first step of panel c) (left) and the second step of panel c) (right) of FIG. 12.

FIG. 13 depicts "organ" shape printing process, illustrating the first step of panel c) (left) and the second step of panel c) (right) of FIG. 12.

FIG. 14 depicts an example of printing an embryoid body-based ink into an embryoid-body based matrix.

Yet a further embodiment relates to a tissue construct produced by the method described herein. The printed tissue construct will comprise one or more tissue patterns, where each tissue pattern comprises a plurality of viable cells of one or more predetermined cell types. A network of vascular channels may interpenetrate the one or more tissue patterns. In certain embodiments, an extracellular matrix composition may at least partially surround the one or more tissue patterns and the network of vascular channels. A pattern or network that "interpenetrates" another pattern or network in a tissue construct may be understood to comprise one or more filaments, channels or portions that are layered with, partially or completely overlapping, partially or completely underlapping, surrounding, embedded within, and/or interwoven with one or more filaments, channels or portions of the other pattern or network. A filament "deposited on a substrate" may be understood to be deposited directly on the substrate or directly on another filament, channel or portion previously deposited or formed on the substrate.

The tissue construct produced by the described method may be a tissue construct with embedded vasculature. Examples of the tissue constructs produced by the described method include heart, artery, vein lymphatic vessel, liver, biliary tract, kidney, pancreas, spleen, lymph node, bone, muscle, brain, spinal cord, nerve, ear, eye, skin, subcutaneous tissue, breast, mammary gland, muscle, tendon, diaphragm, myeloid, lymphoid, nose, nasopharynx, larynx, trachea, bronchus, lung, mouth, salivary gland, tongue, oropharynx, laryngopharynx, esophagus, stomach, small intestine, colon, rectum, anus, genitourinary tract, ureter, bladder, urethra, uterus, vagina, vulva, ovary, placenta, scrotum, penis, prostate testicle, seminal vesicle, pituitary, pineal, thyroid, parathyroid, adrenal, and islets of Langerhans.

Specifically, the tissue construct may be produced by providing a granular tissue; depositing one or more filaments on or in the granular tissue, each filament comprising an ink;

and gelling or fusing the granular tissue, thereby producing the tissue construct, as described above. The step of providing a granular tissue comprises growing a plurality of cells; collecting the plurality of cells; and compacting the cells to form the granular tissue. The granular tissue may then be poured into a mold of arbitrary shape. Alternatively, the granular tissue may be printed onto a substrate or into a mold, allowing for further patterning of the matrix. The depositing step may be to form a functional vascular channel network on or in the granular tissue.

The tissue construct produced by the described method may include up to n different predetermined cell types. For example, n may satisfy $1 \leq n \leq 300$, $2 \leq n \leq 1200$, or $2 \leq n \leq 100$. More typically, n is no more than 50, no more than 30, or no more than 20. For example, there may be 2 or more, 4 or more, 8 or more, 16 or more, or 20 or more predetermined cell types in the tissue construct.

The tissue construct may have any desired 2D or 3D shape. For example, the tissue construct may have a planar geometry constructed from a single layer or multiple layers of cell-laden filaments and an interpenetrating vascular network. Such structures may have any desired height (thickness). Typically, the tissue construct produced by the described method has a height of about 100 cm or less, about 10 cm or less, about 1 cm or less, about 1 mm or less, about 500 microns or less, or about 100 microns or less, and typically at least about 10 microns, at least about 100 microns, at least about 200 microns, or at least about 1 mm.

Alternatively, the tissue construct with embedded vasculature produced by the described method may have an arbitrary or application-dependent 3D size and shape. The tissue construct may have a solid structure, a porous structure, and/or a hollow structure (e.g., tubular or nontubular) and may be fabricated to mimic the morphology and function of particular organ. For example, the tissue construct may have the size and shape of a kidney, heart, pancreas, liver, bladder, vagina, urethra, trachea, esophagus, skin or other bodily organ.

The 3D size and shape may in some cases be determined by a mold, as described above. The mold may hold the granular tissue during the step of depositing filaments and may remain as part of the tissue construct, or it may be removed after processing. In some embodiments, structural filaments may define the perimeter of the tissue construct on the substrate and all or at least a portion of the three-dimensional shape of the tissue construct out of the XY plane. The mold may also have other functionalities besides defining the shape of the tissue construct. For example, the mold may serve as an interface for perfusion of channels in a printed tissue construct.

The tissue construct produced by the methods described herein can be used for suturing into a body and for maturation in vitro. It can also be used in drug toxicity studies, drug screening applications, disease modeling, and for mechanistic studies. Additional uses are also contemplated.

EXAMPLES

Methods:
Media, Ink, and Matrix Formulations

Gelatin sacrificial ink, for embedded printing of vasculature, was prepared from a gelatin stock solution. The stock solution was made by slow addition of 45 g of gelatin into 255 mL of PBS without calcium or magnesium, at 85° C., under stirring. The temperature and stirring was maintained for 12 h to fully dissolve the gelatin, after which the pH was adjusted, while stirring, to ~7.5 using 2N NaOH. The hot gelatin stock solution was sterile filtered, aliquotted, and stored at 4° C. for up to 6 months.

To prepare gelatin sacrificial ink, the gelatin stock solution was first melted at 80° C. for <30 min, then mixed 1:2 with 80° C. PBS without calcium or magnesium, and red food coloring was added at 2% vol/vol to enable visualization of the printing ink.

Silicone ink, for manufacturing tissue molds and perfusion chips, was prepared by combining a 10:1 mass ratio of SE1700:crosslinker (Dow Corning), then adding 2% wt black silicone pigment (Silc-Pig, Smooth-On Inc.). The components were then mixed using a speed-mixer for 3 min at 2000 rpm (Thinky Inc.).

To prepare embryoid body culture medium (EBCM), a stock solution of poly(vinyl-alcohol) (PVA) was prepared by slowly adding 20 g of PVA (Sigma Aldrich) to 100 mL of deionized water, under stirring at room temperature. Next, under continuous stirring, the temperature was increased to 80° C. to complete the dissolution of the PVA, and the temperature was brought back to 37° C. The PVA solution was aliquoted and stored at 4° C. until ready for use. To prepare EBCM, mTeSR1 was mixed 1:50 with the PVA stock solution to generate a ~4 mg/mL solution. Penicillin/streptomycin was added to 100 U/mL, and the solution was sterile filtered and stored at 4° C. for up to two weeks.

The ECM prepolymer gel was prepared immediately prior to harvesting the EBs, or during the harvesting step, as follows:

A transglutaminase working solution was first prepared by adding 20 mg/mL of microbial tissue transglutaminase (TG, MooGlu) to mTeSRI, and sterile-filtering the solution via a 0.2 μm syringe filter. Next, the volume (x mL) of high concentration rat tail collagen I (Corning) required to create a 4 mg/mL collagen concentration in the final ECM solution (total volume y mL) was calculated. The ECM prepolymer gel solution comprises (0.825y–1.135x) mL of mTeSRI, 0.125y mL of TG working solution, x/10 mL of 10×PBS, y/100 mL of 250 mM $CaCl_2$, ~x/40 mL of 1 N NaOH, x mL of high concentration rat tail collagen type 1 and 0.04y mL of matrigel were added, in order. An exemplary recipe is shown in the supplementary methods. The volume of NaOH was adjusted, as necessary, to attain a final pH of ~7.4. After addition and mixing of all components, the gel was centrifuged at 2,000×g for 5 minutes at 2° C. to remove air bubbles. The ECM prepolymer gel was stored on ice until use.

TABLE 1

| Component | Volume (mL) | Order to add |
| --- | --- | --- |
| mTeSR1 | 2.555 | 1 |
| mTeSR1 + 20 mg/mL TG | 1.000 | 2 |
| 10X PBS | 0.360 | 3 |
| $CaCl_2$ 250 mM | 0.080 | 4 |
| NaOH 1M | 0.090 | 5 |
| 8.90 mg/mL Collagen | 3.596 | 6 |
| Matrigel | 0.320 | 7 | iPS Cell Culture

Stocks of human fibroblast-derived Personal Genome Project I (PGPI) induced pluripotent stem cells were stored in CryoVials in liquid nitrogen, with ~300 k PGPI cells/vial, frozen in 0.5 mL of a 1:1 solution of 2× EmbryoMax (EMD Millipore):mTeSRI. To thaw, cells were warmed to 37° C., transferred to a 15 mL centrifuge tube, and fresh 37 C DMEM/F12+HEPES (Thermofisher Scientific) was added dropwise up to 12 mL. The cells were centrifuged at 220×g for 5 minutes, after which the supernatant was aspirated, and the cells were resuspended in 2 mL of mTeSRI (Stem Cell Technologies, Inc) containing 10 µM of ROCK-inhibitor (ROCKi, Y27635), and plated onto a single Matrigel-coated (Corning) well of a 6-well plate. After 24 h, the mTeSRI was replaced to remove the ROCKi. mTeSRI was subsequently replaced daily. Once colonies began to merge (60-80% confluency), cells were rinsed with PBS without calcium or magnesium, and were passaged by adding an enzyme-free passaging solution (ReLeSR) at 1 mL/10 cm$^2$ of tissue culture area. The solution was immediately aspirated away, and the flask incubated for 4.5-5 min at 37° C., 5% $CO_2$. To lift off colonies, 1 mL/10 cm$^2$ of fresh mTeSRI was gently added to the flask using a serological pipette, and pipetted back up once, slowly to break up the colonies. The cells were then added to a freshly prepared flask, performing a split of between 1:8 and 1:3, and mTeSRI was added to a total volume of 2 mL/10 cm$^2$ of tissue culture area. Cells were maintained at 37° C./5% $CO_2$ in an incubator.

Manufacturing of Microwell Arrays

Microwell array plates were used to generate large numbers (>100 k) of highly uniform EBs via forced-aggregation. The microwells, shaped as inverted pyramids with 400 µm base width, were arranged in a 6-well plate format, and manufactured via PDMS molding.

The following process was used to facilitate demolding and ensure casting compatibility between polymers. Briefly, PDMS was poured into a commercially available microwell plate, degassed in a vacuum chamber, and cured at 80° C. for 2 h to generate a negative cast of the microwells. Then, Ecoflex (Smooth-On Inc.) was used to create a positive mold by following a similar method of pouring, degassing and curing as for the PDMS. After removing the cured Ecoflex, a two-part polyurethane (Smooth-On Inc.) was poured onto the Ecoflex positive to create a polyurethane negative mold. Next, ~80 g of Sylgard-184:crosslinker, at a ratio of 10:1, was mixed in an planetary mixer, poured into a polyurethane (Smooth-On) negative mold, degassed for 10 mins in a vacuum, and allowed to cure at room temperature for 48 h. The cured PDMS was then placed in the oven at 80 C for 2 hours to ensure complete crosslinking, and removed from the polyurethane mold.

Embryoid Body Formation

To prepare the wells for cell culture, the wells were immersed in isopropyl alcohol for 1 h, then immersed in water and autoclaved for 1 h. Immediately before preparing the cells, the water was drained from the wells, then the wells were fitted into a sterile one-well tray (Omnitray, Falcon). Next, 1.5 mL of Aggrewell Rinsing Solution (ARS) was added per well before centrifuging the wells at 2,000×g to remove trapped air bubbles from the wells. The ARS was aspirated, and the wells were rinsed 2× with 2 mL DMEM. Finally, the DMEM was replaced with 3 mL of EBCM+10 µM ROCKi, and the wells were maintained at room temperature.

To form EBs, PGPI cells were grown to 60-80% confluency in 225 cm$^2$ T-225 flasks (Falcon). One T-225 of PGPI can be used to seed approximately 24 wells (4×6-well plates) with approximately 500 cells per microwell. To lift-off the PGPI cells from the substrate the cells were first rinsed in PBS without calcium or magnesium, and incubated in Accutase for 15 minutes at 37 C to generate a mostly single-cell suspension. The cells, in Accutase, were added to prewarmed DMEM/F12+HEPES, and centrifuged at 220×g for 5 mins. The supernatant was removed, and cells were resuspended in mTeSRI+10 µM ROCKi media at a volume of 1 mL per well that is to be seeded of. Cells were counted using a live/dead imaging system, and 1 mL of cell suspension was seeded into each well. The wells were finally centrifuged at 100×g for 3 mins to compact the cells. After 24 h, the cell media was replaced with 4 mL of fresh EBCM to remove the ROCKi. The wells then underwent two half-media changes (2 mL of EBCM was replaced with fresh media) per day. Care was taken during media changes, with media added or removed slowly such as to not disturb the EBs from their microwells.

Granular Tissue Formation

Once the EBs measured 200-250 µm in diameter (typically 2-4 d in microwell culture) they were ready for harvesting. Immediately after, or during the preparation of the ECM prepolymer gel, the EBs were harvested via vigorous pipetting up and down in the wells with a P1000 pipette tip, and the EB-containing media was transferred into a 50 mL tube, one tube per 6-wells. The wells were further rinsing with an excess of DMEM/F12+HEPES using a 10 mL serological pipette to remove most (>90%) of the embryoid bodies. The media, with suspended EBs, was added to the 50 mL centrifuge tubes, and the EBs were allowed to settle by incubating on ice for 10 min. All further cell handling is kept on ice to prevent gelation of the ECM prepolymer gel. The supernatant was aspirated and the EBs were collected into a single 50 mL tube on ice. To further wash away single cells, 50 mL of fresh DMEM/F12+HEPES was added, the EBs were allowed to settle for another 10 min, then the supernatant was aspirated and the EBs were resuspended up to 15 mL using DMEM/F12+HEPES and transferred into a 15 mL tube and allowed to settle for 10 min. Next, to compact the EBs, the 15 mL tube was centrifuged at 100×g for 3 min at 2° C., the supernatant was aspirated, and the total volume of the tissue aggregate was estimated. The cells were resuspended in three times their volume in the ECM prepolymer solution by pipetting with a P 1000 pipette, then centrifuged at 100×g and the supernatant was aspirated. Finally, the EB pellet was resuspended in an equal volume of prepolymer ECM solution, forming a dense EB slurry that can be handled and pipetted in subsequent steps.

3D Printing of Silicone Molds

Using a spatula, freshly mixed silicone ink is loaded into a 30 cc syringe (Nordson EFD), and centrifuged at >3,000×g to remove entrapped air. A tapered nozzle with a tip inner-diameter of 0.41 mm (Nordson EFD) is attached to the outlet of the syringe, and the syringe is affixed to a 3D printer, comprising a granite mounted air-bearing gantry that can translate along the x-, y-, and z-axes (Aerotech Inc.). Ink is dispensed from the syringe by means of a pressure generated by an Ultimus V pressure controller (Nordson EFD) onto an underlying glass substrate. The molds are designed using a custom-made MATLAB script that takes geometric inputs from either a .stl, or .bmp file or custom geometric commands, and outputs raw G-code commands for Aerobasic Editor (Aerotech Inc.) to control gantry motion and pressure actuation to produce the silicone walls, and small channels that serve as tube-insertion sites to serve as inlets or outlets to flow. After printing, the silicone is transferred to 80° C. for >2 h to cure the silicone. After curing, fresh silicone ink is extruded onto the top layer of the mold (either manually, or via the 3D printer) and a second glass slide is added to the top, such that the silicone gasket is sandwiched between two glass slides.

Figure 3:
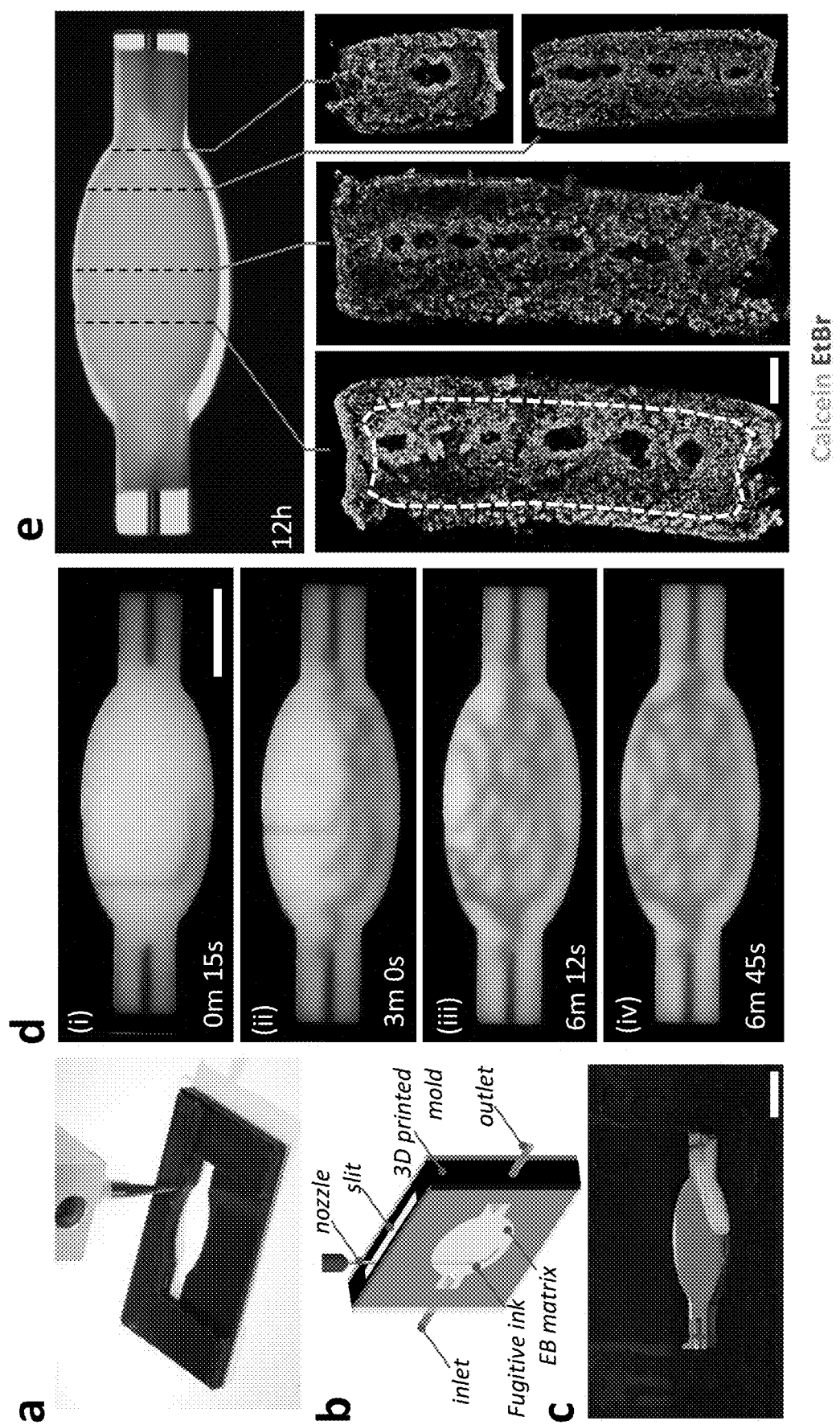
FIG. 3 illustrates through thickness viability of a printed one billion cell perfused construct. (a-b) 3D printed perfusion chip with an integrated inlet and outlet for interfacing with a pump. (c) an image of an exemplary perfusable granular tissue construct. (d) An image sequence showing the embedded 3D printing of a branched, hierarchical vascular network within a compacted embryoid body-based tissue matrix connected to inlet and outlet tubes, seen entering the tissue from the left and right. (e) After 12 h, the printed vessels remained patent (top), and the tissue remained viable throughout its thickness (bottom).

For the mold used in FIG. 3, clear silicone was printed and cured onto the second glass slide, such that the assembled gasket has a slit in the middle of the top side for nozzle insertion (FIG. 3(b)). The mold is transferred to 80° C. to cure the silicone. Molds can be stored at room temperature prior to use.

In addition, as shown in FIG. 17, a modified version of the gasket where gelatin can be first molded within the reservoir and removed after the matrix is casted can be used, in an effort to perfuse the vascularized tissue inside and out.

Embedded Printing of Vasculature

To print vasculature into tissues, freshly prepared sacrificial gelatin ink was loaded into a 0.5 cc glass syringe (Hamilton). Care must be taken to remove all bubbles in the syringe. Next, the syringe was cooled to 4° C. for 15 min to drive the gelation of the ink. The glass syringe was then loaded onto a custom-built syringe pump that is mounted onto the 3D printer. The syringe pump was powered by an Arduino microcontroller and a stepper-motor driver. The syringe barrel was housed in a water-cooled custom-built temperature controller to control the stiffness of the gelatin ink by maintaining an ink temperature of approximately 20° C. A metal nozzle, 1.5" in length and 0.25 mm inner-diameter (Nordson EFD) was fitted to the bottom of the syringe. The syringe was incubated in its temperature controlled housing for >15 min.

Next, the assembled silicone molds were autoclaved and placed onto a custom-made 3D printed housing that holds the mold with its opening vertically upwards and has the footprint of a multiwell plate to enable centrifugation of tissue.

First, if the molds are to be used for perfusion purposes, stainless steel tubes, serving as inlets and outlets with an inner diameter of 0.83 mm are inserted into the inlet/outlet channels of the molds, and versilic silicone tubing, with an inner diameter of $\frac{1}{32}$", is fitted to the external ends of the tubes and crimped with a hose clamp to seal the inlets and outlets.

For the perfusion device in FIG. 3, the stainless-steel tubes had a small ~1 mm notch cut into one end to facilitate a continuous connection from the printed vasculature and the tube. Next molten gelatin sacrificial ink (without red coloring) is added to the mold and the mold is centrifuged at 100×g for 3 mins to remove air bubbles. This step is to lubricate and prevent tissue adhesion into the cracks or indentations of the walls of the mold. After centrifugation, excess molten gelatin is aspirated, leaving behind a thin film on the glass and walls of the mold. To prevent tissue from entering the inlets/outlets during subsequent steps, the metal tubes were flushed with gelatin sacrificial ink (with red coloring), and the molds were placed at 4° C. to drive the gelation of the ink in the channels. Once gelled, the 3D printer can be aligned visually to the metal tubes to ensure the printed vasculature will be contiguous with the inlets and outlets, ensuring a perfusable network. Alignment occurs with the mold housing pressed up against a reference L-bracket that is affixed to the granite of the printer.

After alignment, the EB slurry was loaded into the molds, the following steps were performed rapidly to ensure the slurry remains cold and the ECM does not undergo gelation. The EB slurry was pipetted into the molds, and the molds and their housing were centrifuged at 2° C. for 3 minutes at 100×g to compact the aggregates, forming a granular tissue. The supernatant ECM is aspirated down to ~1 mm above the top of the compacted bed of EBs. If necessary, more EB slurry can be added at this point, centrifuged, and the supernatant aspirated. Next, the mold was transferred onto the front of a custom-built water-cooled metal plate, comprising a metal plate, backed by an acrylic sheet that has been milled with water channels. Both the metal plate and the acrylic sheet were cut to enable back-illumination to facilitate visualization of the printing process. The mold was held on the water-cooled plate by a pair of clamps and is maintained in its housing in a vertical orientation by pressing it against two metal right-triangle prisms.

Next the vasculature was embedded printed, with print speeds ranging from 0.5-4 mm/s. The extrusion rate of the syringe pump was set to define a certain diameter filament. The vascular geometry was designed in a custom-built MATLAB script, that generated branched cubic splines, automatically assigned printing order to prevent the nozzle from cutting through previously printed lines, and rendered each curvilinear line as piecewise linear segments in GCode. To vary the diameter of the filament, the print speed was changed while maintaining a constant extrusion rate. After each line segment, the extrusion would stop, and to avoid agitating the printed patterns, the nozzle would withdraw vertically to above the top of the tissue, translate to its new x- and y-coordinate, and re-insert to the correct new z-coordinate by moving down vertically.

Figure 16:
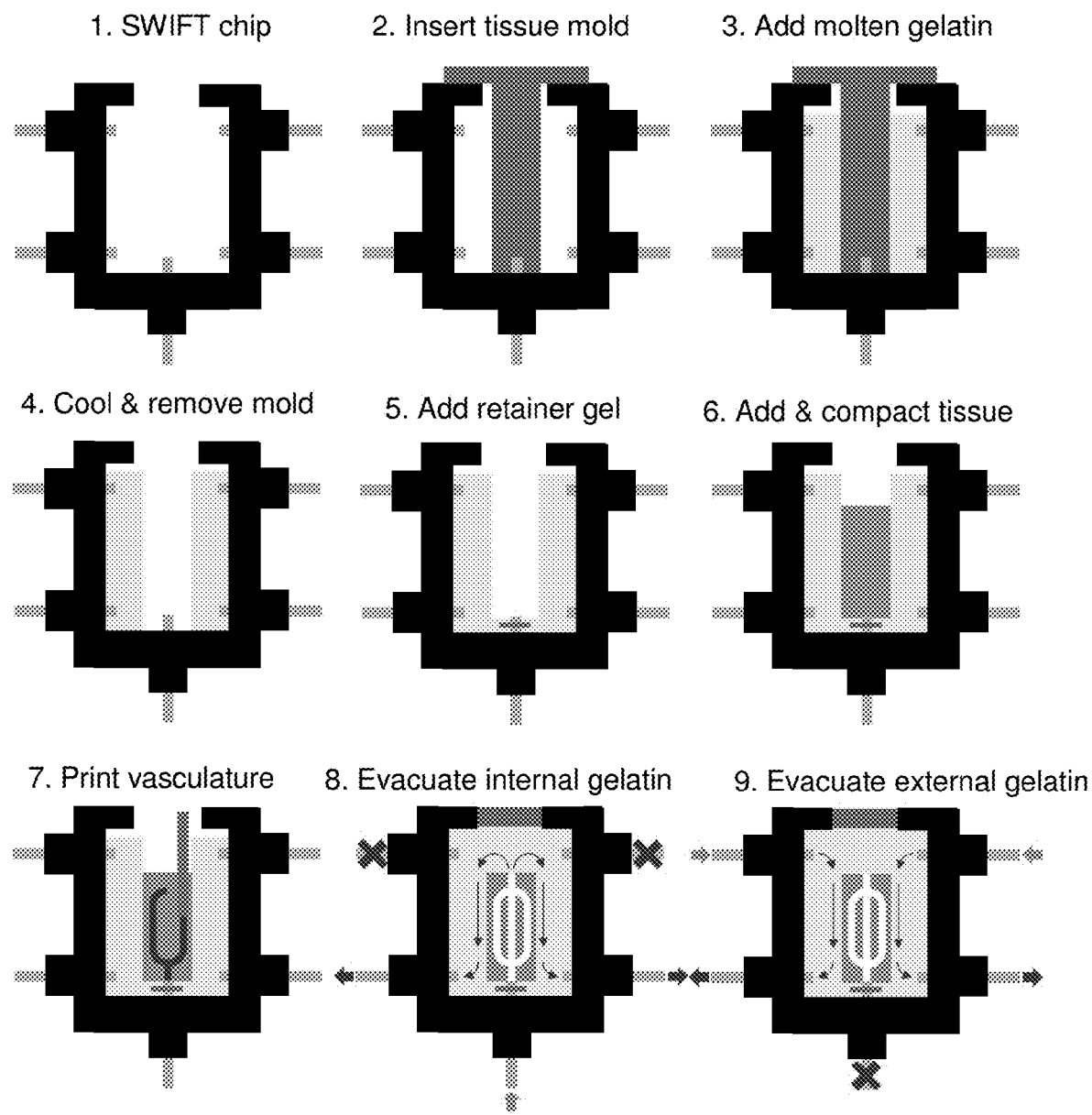
FIG. 16 depicts a schematic of an exemplary manufacturing method of perfusion chips.

When using a modified version of the gasket (FIG. 16), a tissue mold can be inserted into a chip (e.g., SWIFT chip) and molten gelatin added to the chip, which is then cooled, once cooled the tissue mold can be removed. A retainer gel can be added, followed by adding and compacting tissue. The vasculature can them be printed, as shown in FIG. 16(7). The internal gelatin can then be evacuated, followed by evacuation of the external gelatin.

Tissue Perfusion

After printing, the mold was removed from the water-cooled metal plate, and warmed, in air, to room temperature for 20 minutes to facilitate the gelation of the ECM, while maintaining the integrity of the printed sacrificial gelatin filaments. Then, the mold was transferred to a 37° C., 5% $CO_2$ incubator for 20 mins to complete the gelation of the tissue ECM and to melt the printed sacrificial filaments. For tissues that underwent perfusion, the mold was first caulked by extruding an excess of SEI 700 silicone into the gap at the top of the mold, using a pressure dispenser, then was transferred to a custom-made tissue perfusion housing that held the mold vertically and adjacent to 55 cc media reservoirs, containing prewarmed mTeSRI media with 100 U/mL P/S. The inlet pin was first connected to a reservoir via $\frac{1}{32}$" versilic silicone tubing, and the height of the reservoir was adjusted to provide a ~1-3 cm head of water with respect to the tissue outlet to drive evacuation of the fluidized gelatin, until the red food coloring was no longer visibly flowing from the outlet. Next, a constant gravity-driven flow was achieved by re-circulating media at 250 µL/min via a peristaltic pump (Ismatec) from the outlet reservoir to the inlet reservoir, using Pharmed-BPT 2-stop peristaltic tubing with a 1.30 mm inner diameter. The inlet reservoir was hyper-oxygenated by means of bubbling a mixture of sterile-filtered 95% $O_2$/5% $CO_2$ (Airgas Inc.) through the media at a volumetric flow rate of ~20 mL/min.

Microtissue Formation

Two methods were used to generate small-scale, avascular tissues for studying tissue structure and viability.

Figure 4:
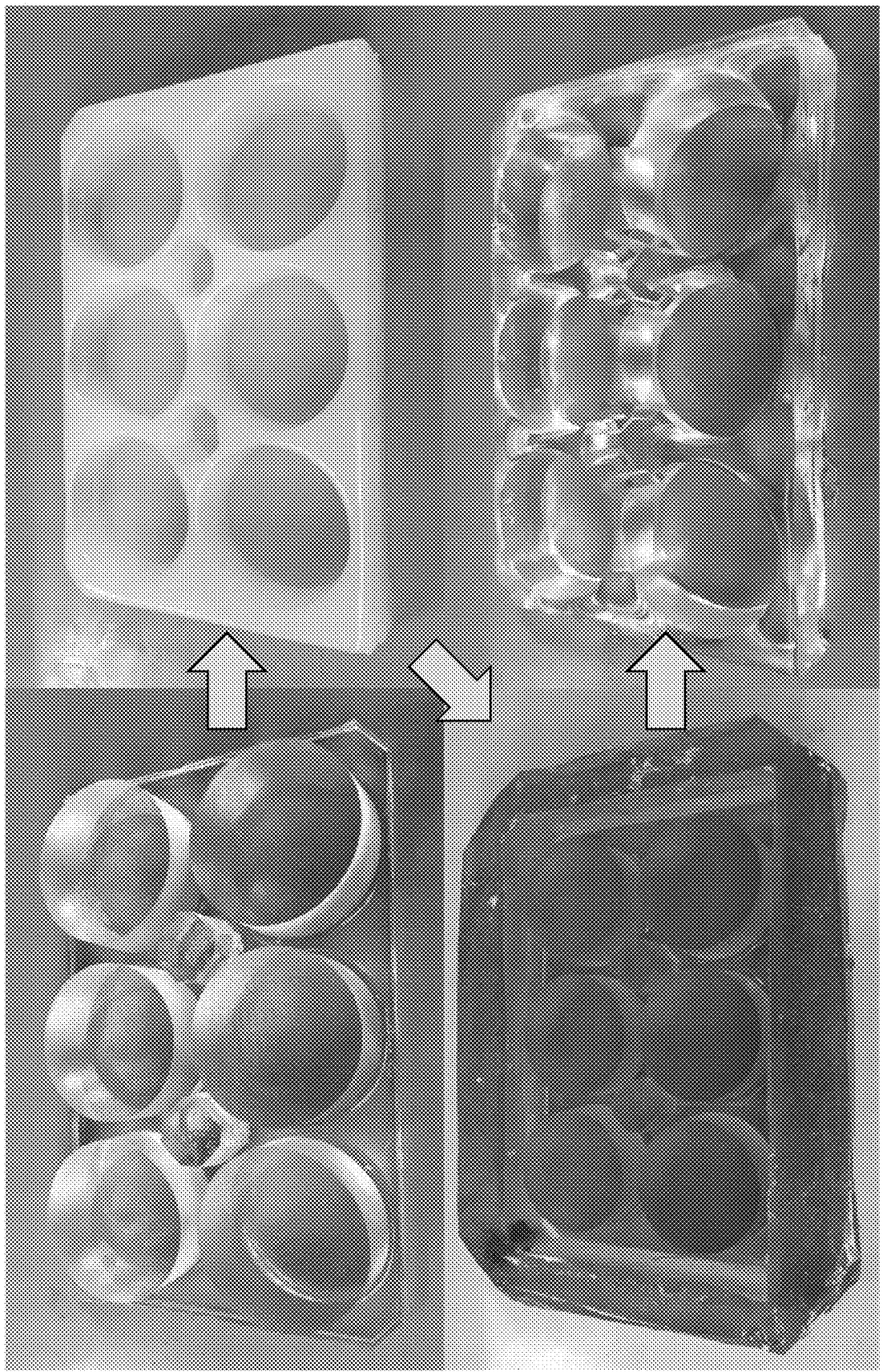
FIG. 4 illustrates embryoid body manufacturing process.

To generate the tissue cubes shown in FIG. 4, cold EB slurry was pipetted into a centrifugation column, comprising a square-shaped well, with a mesh at the bottom to catch EBs and enable the ECM to pass through the mesh, thus compacting the EBs in the column. The tissue was incubated for 20 min at room temperature, then warmed to 37° C. for 20 min to complete gelation. The column was submersed in ice cold media, then delicately removed from the column, and transferred via a cut PI000 pipette tip into a custom-made perfusion basket, comprising an open-topped cube with five walls of polymer mesh to enable open perfusion from all 6 sides of the cube. The basket was placed in a bath of 100 mL mTeSRI with a stir bar and sterile mixture of 95% $O_2$ 5% $CO_2$ was bubbled into the bath. The tissue was incubated for 12 h before performing a cell viability assay.

To manufacture microtissues to study EB packing and for imaging ECM gelation, the EB slurry was pipetted into 3 cc syringe (Nordson EFD) that was pre-cooled to −20° C. The syringe was centrifuged to compact the cells at the bottom, and the supernatant was aspirated down to ~1 mm above the top surface of the compacted EBs. A piston was then inserted into the rear of the syringe, and the air between the compacted EBs and piston was removed by carefully pushing the piston with a blunt rod. Next the EBs were slowly extruded out of the syringe, with no nozzle in place, onto a sheet of silicone with a cylindrical cut-out formed using a biopsy punch. A razor blade was used to remove excess tissue from the top of the mold. The tissue was first incubated at 20 mins at room temperature, then it was transferred into a 37° C. incubator for 20 mins to complete the gelation. After gelation, the tissue was immersed in media, and removed ready for cryosectioning.

Rheology

Figure 8:
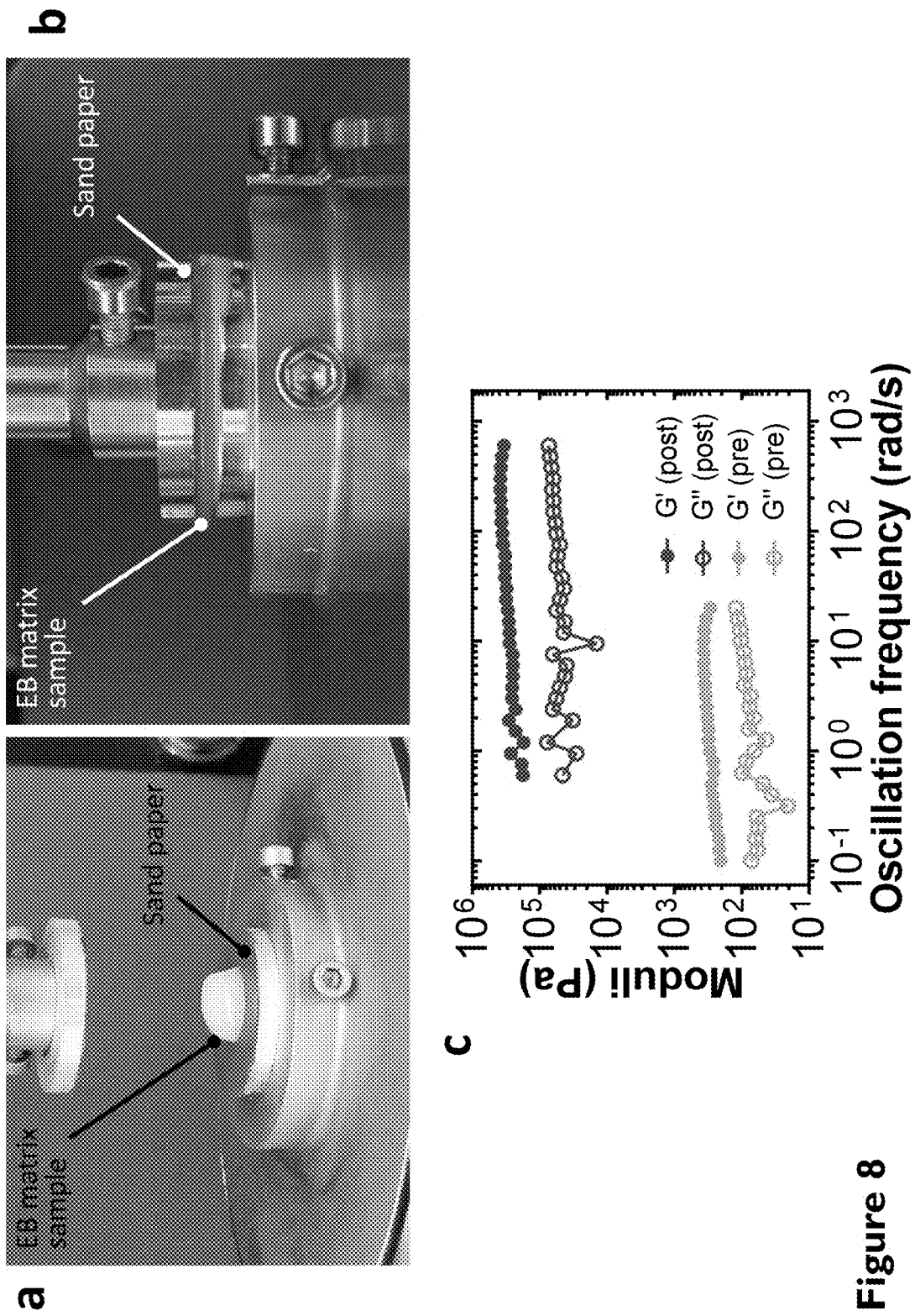
FIG. 8 depicts extra rheology. Optical images of rheological measurement apparatus showing an embryonic body (EB) matrix sample placed on the bottom plate (a) and after the top and bottom plates have been brought together (b). (c) A graph of oscillation frequency and moduli (Pa) measurements.

To characterize the rheology of the EB slurry, the slurry was compacted in a 3 cc syringe, as described above, and extruded directly onto a rheometer plate, cooled to 2 C. Both the plate and disc were coated with sandpaper to prevent slip. Amplitude sweeps, flow curves, and frequency sweeps were measured. See FIG. 8.

Cell Viability Assays

To analyze the tissue containing vessels printed at different print speeds (FIG. 2b,e), after gelling the tissue at 37 C, the tissue was transferred back to 4 C to re-gel the gelatin ink to help prevent vessel collapse during tissue slicing. For perfused EB tissues, the tissues were removed from flow after 12 h of perfusion. In all cases, the tissues and their molds were first immersed in a large bath of ice-cold PBS. The tissues were then cut out from their molds using a scalpel to remove one of the glass slides. Without further disturbing the tissue from its mold, the tissue was sliced using a new scalpel and. Each slice was then transferred from the ice bath via aspiration into a cut 10 mL pipette, and deposited into a 35 mm petri dish. The petri dish had a 5 mm thick silicone press-to-seal sheet on the bottom, with a notch cut to fit the tissue and protect it from flow during handling and media changes. Next, the PBS was changed to mTeSRI media by repeatedly flushing ~50% of the volume at a time. Then, an equal volume of 2× concentrate Live/DEAD solution (1 µL/mL of calcein, 4 µL/mL of ethidium bromide homodimer) was added, and the tissue was incubated at 37 C for 30 mins. After incubation, Live/DEAD images were acquired on a confocal microscope (Zeiss) using a 5× ApoFluor objective.

Cryosectioning and Immunostaining

Tissues were cryosectioned by first fixing for 30 mins in 4% formaldehyde, then rinsed 3× in PBS containing 0.05% Tween20 detergent (PBST). The fixed tissue was incubated overnight at 4° C. in DI water containing 30% sucrose (sucrose solution), then transferred into a 1:1 solution of OCT:sucrose solution for 1 h 30 mins. Next, the tissue was gently placed into a cryostat tissue mold, which was subsequently filled with 100% OCT solution and frozen on a cryostat peltier cooler. The tissue was sectioned using 40 µm slices that were transferred onto a superfrost slide. Sections were stored at −20° C. prior to immunostaining.

The sections were prepared for immunostaining by creating a hydrophobic wall around the tissue section using a PAP pen. Next, the tissues were permeabilized in a 0.125% solution of Triton-X containing 0.5% BSA for 10 mins, rinsed 3× in PBST, and blocked for 30 mins in a solution of PBS containing 3% BSA. After blocking, collagen I antibody was added (Abcam, 1:200 dilution) in PBS containing 3% BSA and incubated overnight at 4° C. The primary antibody was removed by rinsing the tissue 3× in PBST, and a secondary antibody was added at 1:250 for 45 mins, after which it was removed by a further rinsing 3× in PBST. Next, a solution of PBST containing DAPI was added for 5 mins, then rinsed 3× in PBST. Imaging was performed using a Zeiss confocal microscope.

Calculations:

Number of Cells in Organs:

Liver: 140 million cells per gram of liver×1.5 kg=140 billion cells.

Pancreas: 500,000 Islet equivalents are transplanted=6000-8000 islet equivalents per kg of recipient weight. With 3000 cells per islet equivalent (150 um diameter clusters and 10 um cells) billions cells)

Size of the liver if made out of the same cell-laden matrix as in the PNAS paper:150 billion cells at 10 millions cells/ml=15 L liver Example 1

To generate a large number of uniform tissue spheroids, iPSCs were transferred into microwell arrays to form EBs by forced aggregation (FIG. 1a). After four days, these EBs were harvested, mixed with a prepolymer solution of collagen I and matrigel gel, and compacted via centrifugation to form a dense tissue aggregate, comprising approximately 200,000,000 cells per 1 mL of tissue (FIG. 1b). A sacrificial material was then embedded printed to form a three-dimensional vascular network that can interface with an external pump to enable directed perfusion of oxygen and nutrients to maintain viability throughout the bulk of the dense tissue.

It was demonstrated that the culture scale up could generate approximately half a billion cell construct (FIG. 1bi,ii), whose granular microstructure (FIG. 1biii) provide sufficient support for the printing of sacrificial filaments, yet are capable of yielding in front of the translating nozzle and self-healing in its wake (FIG. 1c). These tissue spheroids can take the form of embryoid bodies or any other differentiated aggregates such as cerebral or hepatic organoids or cardiac spheroids (FIG. 1d).

Example 2

Figure 2:
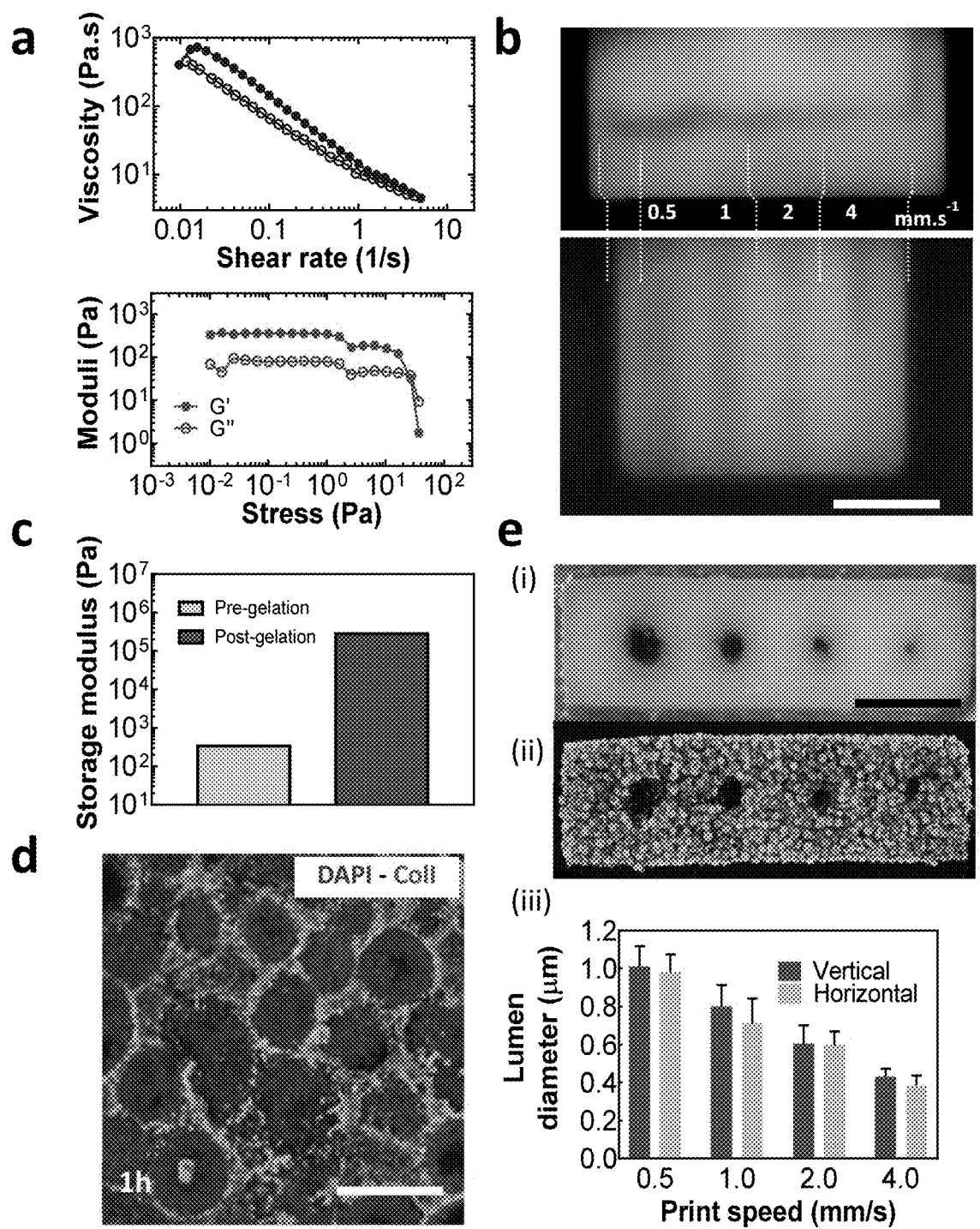
FIG. 2 illustrates printing, gelation and evacuation of vascularized tissue. (a) (top) Apparent viscosity as a function of shear rate and (bottom) shear storage (closed markers) and loss moduli (open markers) as a function of stress of the embryoid body matrix and sacrificial gelatin ink. (b) the described printing of horizontal and vertical features (vascular templates) embedded at print speeds of 0.5, 1, 2, and 4 $mm/s^{-1}$. (c) Storage modulus for pre-gelation and post-gelation. (d) an image of fibrillar gel forming in the space surrounding the embryoid bodies. (e) Effect of print speed on the lumen diameter shown as (i) bright-field and (ii) viability staining images in the context of vertically printed channels and (iii) lumen (channel) diameter as a function of print speed for vascular templates embedded via horizontal and vertical printing.

Quantitatively, the embedded printing was enabled via the shear-thinning, thixotropic, yield-stress rheology of the aggregate tissue (FIG. 2a), capable of supporting embedded 3D printing in both horizontal and vertical directions (FIG. 2b).

After printing, the tissue was warmed to enable gelation of the collagen-matrigel, and a significant stiffening of the matrix was observed (FIG. 2c) as a fibrillar gel forms in the space surrounding the EBs (FIG. 2d). This increased stiffness locks-in the shape of the printed vasculature, and enables pressure-driven flow to permeate the tissue.

Crucial to the generation of hierarchical vascular networks, varying the print speed while maintaining a constant sacrificial material flow rate enabled a smooth variation of vascular diameters (FIG. 2e) while having no adverse effect on the integrity of the EBs.

Example 3

Underscoring the need for the printed vasculature, when cuboidal tissue aggregates are incubated under high-oxygen conditions (95% $O_2$/5% $CO_2$) in a stirred bath infused for 12 h, only the outermost 0.8 mm of tissue remained viable. The core underwent necrosis due to insufficient oxygen and/or nutrient supply.

To enable directed perfusion of the tissue core, 3D printed mold was printed with an integrated inlet and outlet for interfacing with a pump (FIG. 3a,b).

Using this mold, 2.5 mL of aggregate tissue (approximately 400,000 embryoid bodies) was introduced, and a hierarchical vascular network was printed, with varying diameters designed to distribute flow and maintain a constant wall shear stress throughout the network (FIG. 3d). Once the tissue was warmed, gelled, and the sacrificial material evacuated, the tissue was connected to a reservoirs to achieve a smooth gravity-driven flow, with a head height maintained via a recirculating pump. After 12 h, the printed vessels remained patent (FIG. 3e, top), and the tissue remained viable throughout its thickness (FIG. 3e, bottom).

This embedded printing approach enables free-form printing of vasculature into dense tissues, and provides a means to maintain tissue viability in a system with unprecedented scale and cellular density. As a result of the cell density and high viability, it is anticipated that these tissues will exhibit remarkable and surprising levels of function when differentiated.

Example 4

This example illustrates a method for patterning cell aggregates of one or the same type into a matrix comprised of cells of one or the same type.

Specifically, an ink of fluorescently labelled embryoid-bodies (e.g., EB-mKATE2) is printed in the shape of a helix into a matrix of wild-type embryoid bodies (FIG. 14).

Referring to FIG. 14, all cell nuclei are labelled with Hoechst stain (blue). FIG. 14A shows a diagram of the printed cell aggregate helix (red) into the cell-aggregate matrix (yellow). FIG. 14B shows a photograph of the nozzle embedded printing into the matrix. Note that the exit of the nozzle is below the surface of the EB matrix. FIG. 14C shows that after gelation, the patterned tissue can be removed from the holder and sectioned. FIG. 14D shows cross-sectional epifluorescence views of the tissue, demonstrating the helical pattern of printed cells.

This demonstrates that the matrix of compacted cell aggregate, which is normally the bath of tissue in which a sacrificial filament can be printed as a vasculature template, can also serve as an ink itself. This shows that the inventors' ability to "embed print" that compacted cell aggregate material into the similar material. This can lead to a possibility of directly printing that aggregate material as densely cellular filaments.

Example 5

Figure 15:
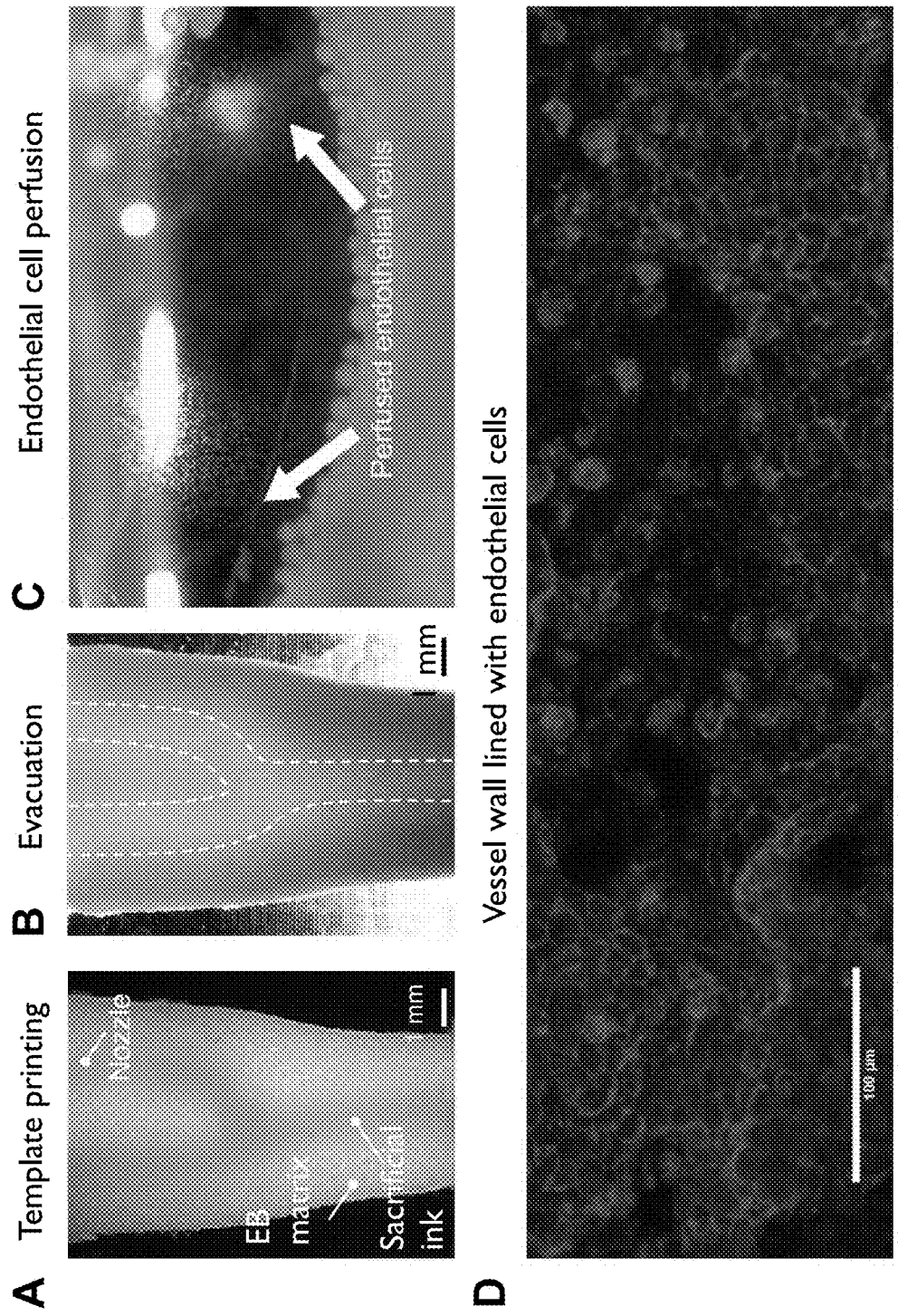
FIG. 15 illustrates template channel endothelialization. (a) A sacrificial ink network is printed. (b) The sacrificial ink is removed, leaving behind a channel. (c) Endothelial cells are flown through the channel network. Endothelial cells are shown exiting the top of the tissue in two streams from the pair of vessels. (d) CD31 stain of endothelium on the surface reveals cobble-stone like architecture of cells, showing the endothelial cell lining.

FIG. 15 illustrates an example of lining vascular channels with endothelial cells. As shown in FIG. 15A, a sacrificial ink network was printed. In FIG. 15B the sacrificial ink was removed, leaving behind a channel. In FIG. 15C endothelial cells were flown through the channel network; endothelial cells are shown exiting the top of the tissue in two streams from the pair of vessels. FIG. 15D shows that CD31 stain of endothelium on the surface reveals cobble-stone like architecture of cells, showing the endothelial cell lining of the vessel wall.

FIG. 15 demonstrates that endothelial cells can be perfused through the templated vasculature and line the walls of the vessels.

All the references are incorporated herein in their entirety:

[1] J. S. Miller, "The Billion Cell Construct: Will Three-Dimensional Printing Get Us There?" PLoS Biol., vol. 12, no. 6, pp. 1-9, June 2014.

[2] K. M. Chrobak, D. R. Potter, and J. Tien, "Formation of perfused, functional microvascular tubes in vitro.," Microvasc. Res., vol. 71, no. 3, pp. 185-96, May 2006.

[3] H. C. Ott et al., "Perfusion-decellularized matrix: using nature's platform to engineer a bioartificial heart.," Nat. Med., vol. 14, no. 2, pp. 213-21, February 2008.

[4] D. B. Kolesky, R. L. Truby, A. S. Gladman, T. A. Busbee, K. A. Homan, and J. A. Lewis, "3D bioprinting of vascularized, heterogeneous cell-laden tissue constructs.," Adv. Mater., vol. 26, no. 19, pp. 3124-30, May 2014.

[5] D. B. Kolesky, K. A. Homan, M. A. Skylar-Scott, and J. A. Lewis, "Three-dimensional bioprinting of thick vascularized tissues," Proc. Natl. Acad. Sci., vol. 113, no. 12, p. 201521342, March 2016.

[6] J. S. Miller et al., "Rapid casting of patterned vascular networks for perfusable engineered three-dimensional tissues.," Nat. Mater., vol. II, no. 9, pp. 768-74, August 2012.

[7] W. Wu, A. Deconinck, and J. A. Lewis, "Omnidirectional printing of 3D microvascular networks," Adv. Mater., vol. 23, no. 24, 2011.

[8] T. J. Hinton et al., "Three-dimensional printing of complex biological structures by freeform reversible embedding of suspended hydrogels," Sci. Adv., vol. 1, no. 9, pp. e1500758-e1500758, 2015.

[9] C. B. Highley, C. B. Rodell, and J. A. Burdick, "Direct 3D Printing of Shear-Thinning Hydrogels into Self-Healing Hydrogels," Adv. Mater., vol. 27, no. 34, pp. 5075-5079, 2015.

[10] M. A. Lancaster et al., "Cerebral organoids model human brain development and microcephaly.," Nature, vol. 501, no. 7467, pp. 373-9, September 2013.

[11] T. Sato et al., "Long-term expansion of epithelial organoids from human colon, adenoma, adenocarcinoma, and Barrett's epithelium," Gastroenterology, vol. 141, no. 5, pp. 1762-1772, 2011.

[12] X. Lian et al., "Robust cardiomyocyte differentiation from human pluripotent stem cells via temporal modulation of canonical Wnt signaling," Proc Natl Acad Sci USA, vol. 109, no. 27, pp. E1848-57, 2012.

[13] E. Vrij, et al., "Directed Assembly and Development of Material-Free Tissues with Complex Architectures," Adv. Mater., vol. 28, pp. 4032-4039, 2016.

[14] M. Itoh et al., "Scaffold-free tubular tissues created by a bio-3D printer undergo remodeling and endothelialization when implanted in rat aortae," PLoS One, vol. 10, no. 9, pp. 1-15, 2015.

Throughout this specification, various indications have been given as to preferred and alternative embodiments of the invention. However, the foregoing detailed description is to be regarded as illustrative rather than limiting and the invention is not limited to any one of the provided embodiments. It should be understood that it is the appended claims, including all equivalents, are intended to define the spirit and scope of this invention.

The invention claimed is:

1. A method of producing a tissue construct, comprising:
compacting embryoid bodies, organoids, cells, cell spheroids, multicellular tissue aggregates, or a combination thereof to form a granular tissue comprising a compacted assembly of embryoid bodies, organoids, cells, cell spheroids, multicellular tissue aggregates, or a combination thereof;
providing the granular tissue;
depositing one or more filaments on or in the granular tissue, each filament comprising an ink; and
gelling or fusing the granular tissue, thereby producing the tissue construct.

2. The method of claim 1, wherein the granular tissue comprises approximately 1,000 to 1 billion cells per mL of the granular tissue.

3. The method of claim 1, wherein the granular tissue comprises cells in the form of single cells, cell aggregates, or both having diameter in the range from about 10 μm to about 5 mm.

4. The method of claim 1, wherein the ink comprises one or more sacrificial ink, cell laden ink, structural ink, conductive ink, optical waveguide ink, or another granular tissue.

5. The method of claim 1, further comprising removing the ink to create one or more open channel or void, and exposing the one or more open channel or void to fluid perfusion.

6. The method of claim 1, wherein the tissue construct comprises a functional vascular channel network.

7. The method of claim 1, wherein the granular tissue further comprises at least one of gelatin, hyaluronic acid, agarose, alginate, poly (ethylene-glycol), native extracellular matrix blends to act as a filler, porogen, drug delivery vehicles, sensors, actuators, photoresponsive elements, or a rheological modifier.

8. The method of claim 1, further comprising the following steps prior to the compacting step:
growing a plurality of cells;
collecting the plurality of cells; and
optionally aggregating the plurality of cells.

9. The method of claim 8, wherein the growing step is on a substrate or in a suspension culture.

10. The method of claim 9, wherein the substrate is a microwell array, and wherein the suspension culture is a non-adherent flask or bioreactor, or hanging drops.

11. The method of claim 8, further comprising pouring the granular tissue into a mold of arbitrary shape.

12. The method of claim 8, further comprising printing the granular tissue onto a substrate or into a mold, allowing for further patterning of a matrix.

13. The method of claim 1, further comprising printing the granular tissue into or onto a supporting matrix, wherein the supporting matrix is another granular tissue, an acellular matrix, or a mixture of the two, allowing for further patterning of the granular tissue construct.

14. The method of claim 13, wherein the supporting matrix comprises at least one of gelatin, hyaluronic acid, agarose, alginate, poly (ethylene-glycol), native extracellular matrix blends to act as a filler, porogen, drug delivery vehicles, sensors, actuators, photoresponsive elements, or a rheological modifier.

15. The method of claim 8, further comprising mixing the cells with an extracellular matrix material solution, wherein the extracellular matrix material solution comprises any natural or synthetic solution capable of residing in an extracellular space of the granular tissue.

16. The method of claim 5, wherein the one or more filaments, flow channels or voids are in communication with one or more external devices.

17. The method of claim 16, wherein the external devices comprise one or more of a pump, a light guide, an actuator, a motor control board, a microcontroller, a data acquisition board, and a field-programmable gate array.

18. The method of claim 1, wherein the filaments form a functional vascular channel network on or in the granular tissue, the functional vascular channel network comprising flow channels or voids in fluid communication with an external pump for direct perfusion of oxygen and nutrients after removal of the ink.

19. The method of claim 5, wherein the step of exposing the one or more open channel or void to fluid perfusion is under a fluid shear stress (FSS).

20. The method of claim 19, wherein the FSS is pulsed to mimic blood pressure changes during regular heart beats.

21. The method of claim 1, further comprising exposing the tissue construct to one or more biological agents, a biological agent gradient, a pressure, and/or an oxygen tension gradient.

22. The method of claim 5, further comprising after removing the ink, injecting a suspension of endothelial cells into the one or more open channels or voids.

23. The method of claim 1, wherein each filament further comprises one or more concentric and coaxial fugitive ink layers.

24. The method of claim 23, wherein the concentric ink layers are arranged as a sacrificial core, a shell comprising smooth muscle cells, and a fibroblast outer shell.

25. The method of any of claim 24, wherein the concentric ink layers are arranged as a sacrificial core, an endothelial cell laden inner shell, a shell comprising smooth muscle cells, and a fibroblast outer shell.

26. The method of claim 5, wherein the step of removing the ink comprises warming the one or more filaments.

27. The method of claim 1, wherein the step of gelling or fusing the granular tissue comprises warming the granular tissue, or exposing the tissue to light to induce crosslinking.

28. The method of claim 1, wherein the one or more filaments are extruded through a single printhead before being deposited on or in the granular tissue.

29. The method of claim 1, wherein the deposited one or more filaments are extruded, and wherein one or more filaments are deposited by extrusion through one or more printheads on or in the granular tissue.

30. The method of claim 1, wherein the depositing is by printing, wherein the print speed is varied while the ink flow is maintained at a constant flow rate, enabling a smooth variation of diameters of the one or more filaments.

31. The method of claim 1, wherein the depositing is by printing, wherein the extrusion rate is varied while the print speed is maintained constant enabling a smooth variation of diameters of the one or more filaments.

32. The method of claim 5, further comprising depositing one or more structural filaments layer by layer on a substrate to form a mold prior to and/or concomitant with the step of providing the granular tissue.

33. The method of claim 32, wherein the mold comprises flow channels in fluid communication with the one or more open channel or void for perfusion thereof after removal of the ink.

34. The method of claim 33, wherein the mold is 3D printed with one or more integrated inlets and outlets for interfacing with a pump.

35. The method of claim 1, wherein the tissue construct is heart, artery, vein lymphatic vessel, liver, biliary tract, kidney, pancreas, spleen, lymph node, bone, muscle, brain, spinal cord, nerve, ear, eye, skin, subcutaneous tissue, breast, mammary gland, muscle, tendon, diaphragm, myeloid, lymphoid, nose, nasopharynx, larynx, trachea, bronchus, lung, mouth, salivary gland, tongue, oropharynx, laryngopharynx, esophagus, stomach, small intestine, colon, rectum, anus, genitourinary tract, ureter, bladder, urethra, uterus, vagina, vulva, ovary, placenta, scrotum, penis, prostate testicle, seminal vesicle, pituitary, pineal, thyroid, parathyroid, adrenal, and islets of Langerhans.

36. The method of claim 35, wherein the tissue construct is for use as a tissue graft for suturing into a patient's body, for maturation in vitro, in studying drug toxicity, in drug screening, in disease modeling, or in mechanistic studies.

* * * * *

UNITED STATES PATENT AND TRADEMARK OFFICE
CERTIFICATE OF CORRECTION

PATENT NO. : 12,296,069 B2
APPLICATION NO. : 16/649056
DATED : May 13, 2025
INVENTOR(S) : Mark Skylar-Scott, Sebastien Uzel and Jennifer Lewis It is certified that error appears in the above-identified patent and that said Letters Patent is hereby corrected as shown below:

In the Specification

In Column 7, Line 57, delete "1K-1 BB" and replace with --1K-1BB--.

In Column 14, Line 50, delete "beta" and replace with --beta1--.

In Column 14, Line 51, delete "(TGF beta I)" and replace with --(TGF beta1)--.

In Column 18, Lines 22, 37, 64; Column 19, Lines 2, 5, 6, 13, 17; Column 22, Line 42; Column 23, Line 4, delete "mTeSRI" and replace with --mTeSR1--.

In Column 18, Line 61, delete "Project I (PGPI)" and replace with --Project 1 (PGP1)--.

In Column 18, Line 62, delete "-300 k PGPI" and replace with --~300 k PGP1--.

In Column 19, Lines 57 and 60, delete "PGPI" and replace with --PGP1--.

In Column 22, Line 55, delete "-20" and replace with --~20--.

In Column 22, Line 67, delete "PI000" and replace with --P1000--.

Signed and Sealed this
Fourteenth Day of October, 2025

John A. Squires
*Director of the United States Patent and Trademark Office*